United States Patent [19]

Riedl et al.

[11] Patent Number: 5,792,765
[45] Date of Patent: Aug. 11, 1998

[54] SUBSTITUTED OXAZOLIDINONES

[75] Inventors: Bernd Riedl; Dieter Häbich; Andreas Stolle; Martin Ruppelt, all of Wuppertal; Stephan Bartel, Bergisch Gladbach; Walter Guarnieri, Zülpich; Rainer Endermann; Hein-Peter Kroll, both of Wuppertal, all of Germany

[73] Assignee: Bayer Aktiengesellschaft, Leverkusen, Germany

[21] Appl. No.: 794,034

[22] Filed: Feb. 3, 1997

[30] Foreign Application Priority Data

Feb. 6, 1996 [DE] Germany ............... 19604223.2

[51] Int. Cl.$^6$ .................. A61K 31/42; C07D 413/14
[52] U.S. Cl. .................. 514/236.8; 546/256; 546/271.4; 546/208; 544/324; 544/405; 544/238; 544/369; 544/137; 548/215; 548/235; 548/196; 548/171; 548/178; 514/340; 514/256; 514/252; 514/331; 514/365; 514/367; 514/374
[58] Field of Search ............... 546/256, 271.4, 546/208; 544/324, 405, 238, 369, 137; 548/215, 235, 196, 171, 178; 514/340, 256, 252, 331, 236.8, 365, 367, 374

[56] References Cited

U.S. PATENT DOCUMENTS

| 4,705,799 | 11/1987 | Gregory ............... 514/376 |
| 4,801,600 | 1/1989 | Wang et al. ............... 514/376 |
| 4,942,183 | 7/1990 | Gregory et al. ............... 514/376 |
| 4,965,268 | 10/1990 | Wang et al. ............... 514/253 |
| 5,032,605 | 7/1991 | Wang et al. ............... 514/376 |
| 5,164,510 | 11/1992 | Brickner ............... 548/231 |
| 5,254,577 | 10/1993 | Carlson et al. ............... 514/376 |
| 5,475,014 | 12/1995 | Akasaka et al. ............... 514/367 |
| 5,529,998 | 6/1996 | Habich et al. ............... 514/233.8 |
| 5,561,148 | 10/1996 | Gante et al. ............... 514/376 |
| 5,574,055 | 11/1996 | Borgulya et al. ............... 514/376 |

FOREIGN PATENT DOCUMENTS

| 352781 | 1/1990 | European Pat. Off. . |
| 609441 | 8/1994 | European Pat. Off. . |
| 693491 | 1/1996 | European Pat. Off. . |
| 694543 | 1/1996 | European Pat. Off. . |
| 4425609 | 1/1996 | Germany . |

OTHER PUBLICATIONS

E.A. ter Laak, Antimicrobial Agents and Chemotherapy, vol. 35, No. 2, pp. 228–233 (1991).

J. Swenson et al, Antimicrobial Agents and Chemotherapy, vol. 21, No. 2, pp. 182–192 (1982).

C. Park et al. J.Med.Chem., vol. 35, pp. 1156–1165 (1992).

*Primary Examiner*—José G. Dees
*Assistant Examiner*—Laura R. C. Lutz
*Attorney, Agent, or Firm*—Sprung Kramer Schaefer & Briscoe

[57] ABSTRACT

The present invention relates to new substituted oxazolidinones of the general formula (1)

(I)

in which the substituents have the meaning indicated in the description, processes for their preparation and their use as medicaments, in particular as antibacterial medicaments.

9 Claims, No Drawings

SUBSTITUTED OXAZOLIDINONES

The present invention relates to new substituted oxazolidinones, processes for their preparation and their use as medicaments, in particular as antibacterial medicaments.

The publications U.S. Pat. Nos. 5,254,577, 4,705,799, EP 311 090, EP 312 000 and C. H. Park et al., J. Med. Chem. 35, 1156 (1992) disclose N-aryloxazolidinones having antibacterial action. Additionally, 3-(nitrogen-substituted) phenyl-5-beta-amidomethyloxazolidin-2-ones are disclosed in EP 609 905 A1.

Furthermore, oxazolidinone derivatives having a monoamine oxidase-inhibitory action are published in EP 609 441 and EP 657 440 and those having action as adhesion receptor antagonists are published in EP 645 376.

Antibacterially active oxazolidinone derivatives are also described in our applications EP 694 543, EP 693 491, EP 694 544, EP 697 412 and EP 738 726.

The present invention relates to new substituted oxazolidinones of the general formula (I)

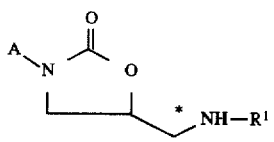

in which

A represents a 5-membered aromatic heterocycle bonded directly via a carbon atom and having up to 3 heteroatoms from the series S, N and/or O, which can additionally have a fused benzene or naphthyl ring, or represents a 6-membered, aromatic heterocycle bonded directly via a carbon atom and having at least one nitrogen atom, or represents an in each case 6-membered, bi- or tricyclic aromatic radical bonded directly via a carbon atom and having at least one nitrogen-containing ring, or represents β-carbolin-3-yl or indolizinyl bonded directly via the 6-membered ring, the cyclic systems optionally in each case being substituted up to 3 times in an identical or different manner by carboxyl, halogen, cyano, mercapto, formyl, phenyl, trifluoromethyl, nitro, straight-chain or branched alkoxy, alkoxycarbonyl, alkylthio or acyl each having up to 6 carbon atoms or by straight-chain or branched alkyl or alkenyl each having up to 6 carbon atoms, which for their part can be substituted by phenyl, and/or being substituted by pyridyl, which for its part can be substituted by straight-chain alkyl or alkoxy each having up to 6 carbon atoms or represents a radical of the formula

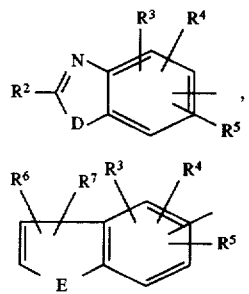

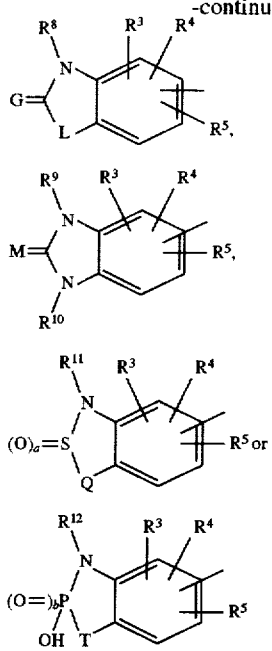

in which $R^3$, $R^4$, $R^5$, $R^6$ and $R^7$ are identical or different and denote hydrogen or carboxyl, halogen, cyano, formyl, trifluoromethyl, nitro, straight-chain or branched alkyl having up to 6 carbon atoms or a group of the formula —CO—NR $^3$R$^{14}$, in which $R^{13}$ and $R^{14}$ are identical or different and denote hydrogen, straight-chain or branched alkyl having up to 4 carbon atoms or phenyl, $R^2$, $R^8$, $R^9$, $R^{10}$, $R^{11}$ and $R^{12}$ are identical or different and denote hydrogen, cycloalkylcarbonyl or cycloalkyl each having 3 to 6 carbon atoms, or straight-chain or branched alkoxycarbonyl or alkylthio each having up to 6 carbon atoms, or denote straight-chain or branched alkyl having up to 10 carbon atoms, which is optionally substituted by cyano, trifluoromethyl, halogen, phenyl, hydroxyl, carboxyl, straight-chain or branched alkoxycarbonyl having up to 6 carbon atoms, aryl having 6 to 10 carbon atoms, cycloalkyl having 3 to 6 carbon atoms and/or by a group of the formula —(CO)$_e$—NR$^{15}$R$^{16}$, $R^{17}$—N—SO$_2$—R$^{18}$, R$^{19}$R$^{20}$—N—SO$_2$— or R$^{21}$—S(O)$_d$, in which c denotes a number 0 or 1, $R^{15}$, $R^{16}$ and $R^{17}$ have the meaning of $R^{13}$ and $R^{14}$ indicated above and are identical to or different from this, or together with the nitrogen atom form a 5- to 6-membered, saturated heterocycle optionally having a further heteroatom from the series N, S and/or O, which for its part can be optionally substituted, also on a further nitrogen atom, by straight-chain or branched alkyl or acyl having up to 3 carbon atoms, $R^{19}$ and $R^{20}$ have the meaning of $R^{13}$ and $R^{14}$ indicated above and are identical to or different from this, d denotes a number 0, 1 or 2, $R^{18}$ and $R^{21}$ are identical or different and denote straight-chain or branched alkyl having up to 4 carbon atoms, benzyl, phenyl or tolyl, or denote straight-chain or branched acyl having up to 6 carbon atoms, which is optionally substituted by trifluoromethyl, trichloromethyl or by a group of the formula —OR$^{22}$, in which $R^{22}$ denotes hydrogen or straight-chain or branched alkyl having up to 6 carbon atoms, which is optionally substituted by aryl having up to 10 carbon atoms, or denotes a group of the formula —(CO)$_e$—NR$^{23}$R$^{24}$, —NR$^{25}$—SO$_2$R$^{26}$, R$^{27}$R$^{28}$—NSO$_2$— or R$^{29}$—S(O)$_f$ in which e has the meaning of c indicated above and is identical to or different from this, $R^{23}$ and $R^{24}$ and $R^{25}$ each have the meaning of $R^{15}$, $R^{16}$ and $R^{17}$ indicated above and are identical to or different from this, $R^{27}$ and $R^{28}$ have the meaning of $R^{13}$ and $R^{14}$ indicated above and are identical to or different from this, f has the meaning of d indicated above and is identical to or different from this, $R^{26}$ and $R^{29}$ have the meaning of $R^{18}$ and $R^{21}$ in each case indicated above and are identical to or different from this, D denotes an oxygen atom or a radical of the formula —S(O)$_g$, in which g denotes a number 0, 1 or 2, E and L are identical or different and denote an oxygen or a sulphur atom, G, M, T and Q are identical or different and denote an oxygen or a sulphur atom, or a group of the formula —NR$^{30}$, in which $R^{30}$ denotes hydrogen or straight-chain or branched alkyl having up to 5 carbon atoms, a and b are identical or different and denote a number 1 or 2, $R^1$ represents a radical of the formula

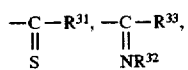

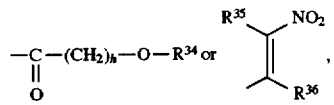

in which $R^{31}$ denotes straight-chain or branched alkyl having up to 7 carbon atoms, cycloalkyl having 3 to 6 carbon atoms, phenyl or a group of the formula in which $R^{38}$ and $R^{39}$ have the meaning of $R^{13}$ and $R^{14}$ indicated above and are identical to or different from this, $R^{32}$ denotes hydrogen, cyano, cycloalkyl having 3 to 6 carbon atoms, phenyl or straight-chain or branched alkyl having up to 7 carbon atoms, $R^{33}$ denotes hydrogen, straight-chain or branched alkyl having up to 7 carbon atoms, phenyl, cycloalkyl having 3 to 6 carbon atoms or a group of the formula —NR$^{40}$R$^{41}$, in which $R^{40}$ and $R^{41}$ have the meaning of $R^{13}$ and $R^{14}$ indicated above and are identical to or different from this, h denotes a number 1, 2, 3 or 4, $R^{34}$ denotes hydrogen, straight-chain or branched alkyl having up to 6 carbon atoms or benzyl, $R^{35}$ and $R^{36}$ are identical or different and denote hydrogen or straight-chain or branched alkyl having up to 6 carbon atoms, or $R^1$ represents cyano or a 5- to 7-membered, saturated, partially unsaturated or unsaturated heterocycle having up to 3 heteroatoms from the series S, N and/or O, which is optionally substituted, also via an N function, up to 2 times in an identical or different manner by benzyl, halogen or by straight-chain or branched alkyl having up to 5 carbon atoms, and their salts.

Physiologically acceptable salts of the substituted oxazolidinones can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts which may be mentioned are salts with customary bases, such as, for example, alkali metal salts (e.g. sodium or potassium salts), alkaline earth metal salts (e.g. calcium or magnesium salts) or ammonium salts, derived from ammonia or organic amines such as, for example, diethylamine, triethylamine, ethyldiisopropylamine, procaine, dibenzylamine, N-methylmorpholine, dihydroabietylamine, 1-ephenamine or methyl-piperidine.

Reaction products with $C_1$–$C_4$-alkyl halides, in particular with $C_1$–$C_4$-alkyl iodides, can additionally function as salts.

Heterocycle in general represents a 5- to 6-membered, saturated or unsaturated ring, which as heteroatoms can contain up to 3 oxygen, sulphur and/or nitrogen atoms. The following are mentioned preferably: thienyl, furyl, pyrrolyl, pyrazolyl, pyridyl, pyrimidyl, pyrazinyl, pyridazinyl, thiazolyl, oxazolyl, imidazolyl, pyrrolidinyl, piperidinyl or piperazinyl.

These also include 5- to 6-membered saturated heterocycles bonded via N, which additionally can contain up to 2 oxygen, sulphur and/or nitrogen atoms as heteroatoms, such as, for example, piperidyl, morpholinyl or piperazinyl or pyrrolidinyl. Piperidyl, morpholinyl and pyrrolidinyl are particularly preferred.

Hydroxyl protective group in the context of the definition given above in general represents a protective group from the series: trimethylsilyl, triisopropylsilyl, tert-butyldimethylsilyl, benzyl, benzyloxycarbonyl, 2-nitrobenzyl, 4-nitrobenzyl, tert-butyloxycarbonyl, allyloxycarbonyl, 4-methoxybenzyl, 4-methoxybenzyloxycarbonyl, tetrahydropyranyl, formyl, acetyl, trichloroacetyl, 2,2,2-trichloroethoxycarbonyl, methoxyethoxymethyl, [2-(trimethylsilyl)ethoxy]methyl, benzoyl, 4-methylbenzoyl, 4-nitrobenzoyl, 4-fluorobenzoyl, 4-chlorobenzoyl or 4-methoxybenzoyl. Acetyl, tert-butyldimethylsilyl and tetrahydropyranyl are preferred.

Amino protective groups in the context of the invention are the customary amino protective groups used in peptide chemistry.

These preferably include: benzyloxycarbonyl, 2,4-dimethoxybenzyloxycarbonyl, 4-methoxybenzyloxycarbonyl, methoxycarbonyl, ethoxycarbonyl, tert-butoxycarbonyl, allyloxycarbonyl, phthaloyl, 2,2,2-trichloroethoxycarbonyl, fluorenyl-9-methoxycarbonyl, formyl, acetyl, 2-chloroacetyl, 2,2,2-trifluoroacetyl, 2,2,2-trichloroacetyl, benzoyl, 4-chlorobenzoyl, 4-bromobenzoyl, 4-nitrobenzoyl, phthalimido, isovaleroyl or benzyloxymethylene, 4-nitrobenzyl, 2,4-dinitrobenzyl, 4-nitrophenyl, 4- methoxyphenyl or triphenylmethyl.

The compounds according to the invention can exist in stereoisomeric forms which either behave as image and mirror image (enantiomers), or which do not behave as image and mirror image (diastereomers). The invention relates both to the enantiomers or diastereomers and their respective mixtures. Like the diastereomers, the racemic forms can also be separated into the stereoisomerically homogeneous constituents in a known manner.

Preferred compounds of the general formula (1) are those in which

A represents quinolyl, benzothiophenyl, benzothiazolyl, benzoxazolyl, pyridyl, pyridazyl or thienyl, each bonded via a carbon atom, each of which is optionally substituted up to 3 times in an identical or different manner by fluorine, chlorine, bromine, phenyl or by straight-chain or branched alkyl or alkylthio each having up to 4 carbon atoms or by straight-chain or branched alkenyl having up to 4 carbon atoms, which for its part can be substituted by phenyl, and/or is substituted by pyridyl, which for its part can be substituted by straight-chain or branched alkyl or alkoxy each having up to 5 carbon atoms, or represents a radical of the formula

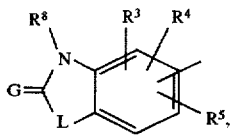

in which

G denotes an oxygen or sulphur atom,

L denotes an oxygen or sulphur atom, $R^8$ denotes straight-chain or branched alkyl or alkylthio each having up to 6 carbon atoms, $R^3$, $R^4$ and $R^5$ are identical or different and denote hydrogen, fluorine, chlorine or bromine, $R^1$ represents a radical of the formula

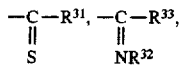

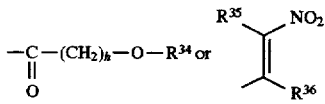

in which $R^{31}$ denotes straight-chain or branched alkyl having up to 5 carbon atoms, cyclopropyl, cyclobutyl, cyclopentyl, cyclohexyl, phenyl or a group of the formula —$NR^{38}R^{39}$, in which $R^{38}$ and $R^{39}$ are identical or different and denote hydrogen, methyl or ethyl, $R^{32}$ denotes hydrogen, cyano, cyclopropyl, cyclobutyl, cyclopentyl, cyclohexyl, phenyl or straight-chain or branched alkyl having up to 5 carbon atoms, $R^{33}$ denotes hydrogen, straight-chain or branched alkyl having up to 5 carbon atoms, phenyl, cyclopropyl, cyclobutyl, cyclopentyl, cyclohexyl or a group of the formula —$NR^{40}R^{41}$, in which $R^{40}$ and $R^{41}$ have the meaning of $R^{38}$ and $R^{39}$ given above and are identical to or different from this, h denotes a number 1, 2, 3 or 4, $R^{34}$ denotes hydrogen, straight-chain or branched alkyl having up to 4 carbon atoms or benzyl, $R^{35}$ and $R^{36}$ are identical or different and denote hydrogen or straight-chain or branched alkyl having up to 4 carbon atoms, or $R^1$ represents cyano or thienyl, oxazolyl, thiazolyl, isoxazolyl or pyrazolyl, each of which is optionally substituted, also via an N function, up to 2 times in an identical or different manner by benzyl, fluorine, chlorine, bromine or by straight-chain or branched alkyl having up to 3 carbon atoms, and their salts.

Particularly preferred compounds of the general formula (1) according to the invention are those in which A represents quinolyl, benzothiophenyl, benzothiazolyl, benzoxazolyl, pryidyl, pyridazyl or thienyl, each bonded via a carbon atom, each of which is optionally substituted up to 2 times in an identical or different manner by fluorine, chlorine, bromine, phenyl, by straight-chain or branched alkyl or alkylthio each having up to 3 carbon atoms or by straight-chain or branched alkenyl having up to 3 carbon atoms, which for its part can be substituted by phenyl, and/or is substituted by pyridyl, which for its part can be substituted by straight-chain or branched alkyl or alkoxy each having up to 4 carbon atoms, or represents a radical of the formula

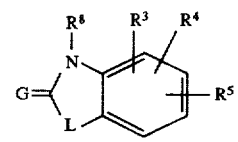

in which

G denotes an oxygen or sulphur atom,

L denotes an oxygen or sulphur atom, $R^8$ denotes straight-chain or branched alkyl having up to 4 carbon atoms, $R^3$, $R^4$ and $R^5$ are identical or different and denote hydrogen, fluorine, chlorine or bromine, $R^1$ represents a radical of the formula

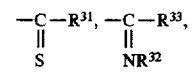

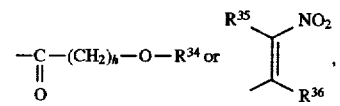

in which $R^{31}$ denotes straight-chain or branched alkyl having up to 4 carbon atoms, cyclopropyl, cyclobutyl, cyclopentyl, cyclohexyl, phenyl or a group of the formula —$NR^{38}R^{39}$, in which $R^{38}$ and $R^{39}$ are identical or different and denote hydrogen or methyl, $R^{32}$ denotes hydrogen, cyano, cyclopropyl, cyclobutyl, cyclopentyl, cyclohexyl, phenyl or straight-chain or branched alkyl having up to 4 carbon atoms, $R^{33}$ denotes hydrogen, straight-chain or branched alkyl having up to 4 carbon atoms, phenyl, cyclopropyl, cyclobutyl, cyclopentyl, cyclohexyl or a group of the formula —$NR^{40}R^{41}$, in which $R^{40}$ and $R^{41}$ have the meaning of $R^{38}$ and $R^{39}$ given above and are identical to or different from this, h denotes a number 1, 2, 3 or 4, $R^{34}$ denotes hydrogen, straight-chain or branched alkyl having up to 3 carbon atoms or benzyl, $R^{35}$ and $R^{36}$ are identical or different and denote hydrogen or straight-chain or branched alkyl having up to 3 carbon atoms, or $R^1$ represents cyano or thienyl, thiazolyl, isoxazolyl or pyrazolyl, each of which can optionally be substituted also, via an N function, up to 2 times in an identical or different manner by benzyl, fluorine, chlorine, bromine or by straight-chain or branched alkyl having up to 3 carbon atoms, and their salts.

Furthermore particularly preferred compounds of the general formula (I) are those in which A represents quinolyl, pyridyl or pyridazyl, each bonded via a carbon atom, each of which is substituted as indicated above.

Furthermore particularly preferred compounds of the general formula (I) are those in which A represents benzothiophenyl or thienyl, each bonded via a carbon atom, each of which is optionally substituted as indicated above.

Furthermore particularly preferred compounds of the general formula (I) are those in which A represents benzothiazolyl or benzoxazolyl, each bonded via a carbon atom, each of which is optionally substituted as indicated above.

Furthermore particularly preferred compounds of the general formula (I) are those in which A represents a radical of the formula

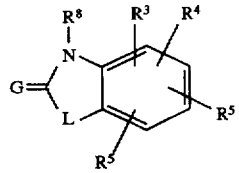

in which $R^3$, $R^4$, $R^5$ and $R^8$ can have the meanings indicated above.

Furthermore particularly preferred compounds of the general formula (I) are those in which $R^1$ represents a radical of the formula

in which $R^{31}$ is as defined above.

Furthermore particularly preferred compounds of the general formula (I) are those in which $R^1$ represents a radical of the formula

in which $R^{32}$ and $R^{33}$ are as defined above.

Furthermore particularly preferred compounds of the general formula (I) are those in which $R^1$ represents a radical of the formula

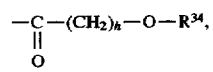

in which h and $R^{34}$ are as defined above.

Furthermore particularly preferred compounds of the general formula (I) are those in which $R^1$ represents a radical of the formula

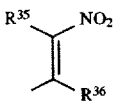

in which $R^{35}$ and $R^{36}$ are as defined above.

Furthermore particularly preferred compounds of the general formula (I) are those in which $R^1$ represents cyano or thienyl, thiazolyl, isoxazolyl or pyrazolyl, each of which can optionally be substituted, also via an N function, up to 2 times in an identical or different manner by benzyl, fluorine, chlorine, bromine or by straight-chain or branched alkyl having up to 3 carbon atoms.

A process for the preparation of the compounds of the general formula (I) according to the invention has additionally been found, characterized in that

[A] compounds of the general formula (II)

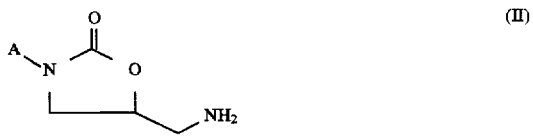

in which

A has the meaning indicated above, are reacted with compounds of the general formula (III)

$$R^1-Y \qquad (III)$$

in which $R^1$ has the meaning indicated above, and

Y, depending on $R^1$, represents hydrogen, halogen or $C_1-C_4$ straight-chain or branched alkoxy or oxyalkoxycarbonyl, or

[B] compounds of the general formula (IV)

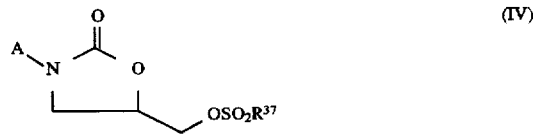

in which

A has the meaning indicated above, $R^{37}$ represents $C_1-C_4$-alkyl, are reacted with compounds of the general formula (V)

$$NH_2-R^{1'} \qquad (V)$$

in which $R^{1'}$ represents one of the heterocycles listed above under $R^1$, or with ethyl dithioacetate in inert solvents, if appropriate in the presence of a base, and in the case of the S-oxides an oxidation is carried out according to a customary method, and, if appropriate, further substituents or functional groups already present are introduced or derivatized according to customary methods, such as, for example, alkylation, redox reactions, substitution reactions and/or hydrolysis or incorporation and decomposition of protective groups.

The processes according to the invention can be illustrated by way of example by the following equations:

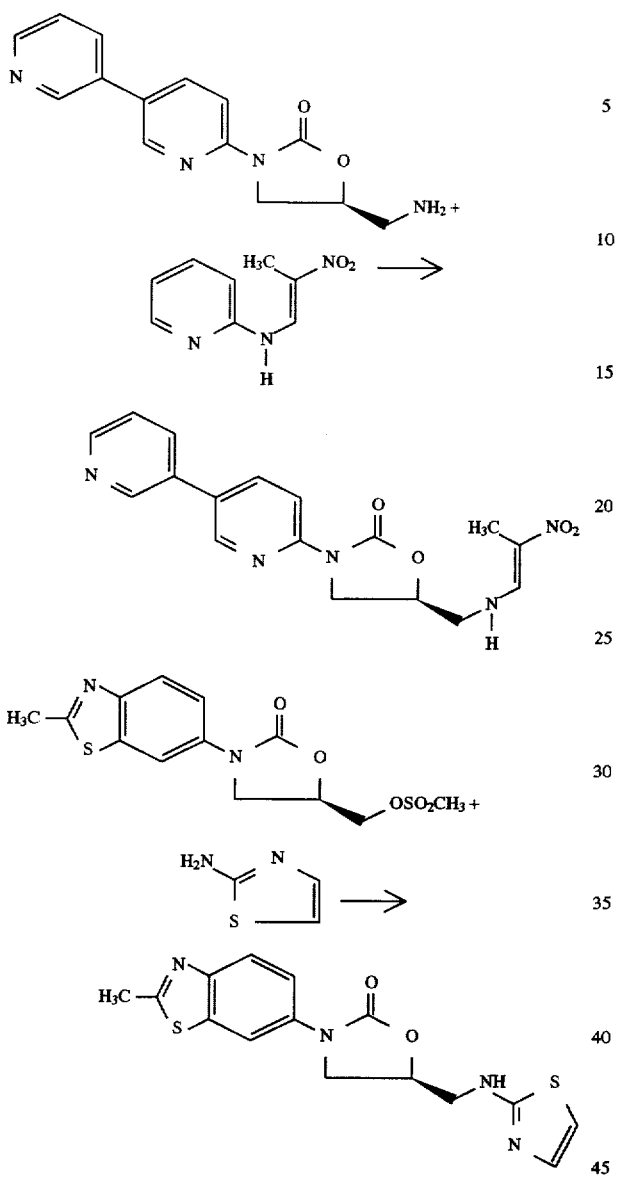

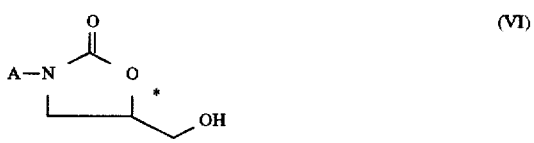

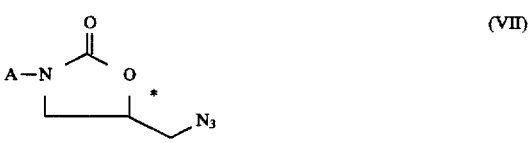

Suitable solvents, depending on the individual process steps, are the customary solvents which do not change under the reaction conditions.

These preferably include alcohols such as methanol, ethanol, propanol or isopropanol, or ethers such as diethyl ether, dioxane, 1,2-dimethoxyethane, tetrahydrofuran, glycol dimethyl ether or tert-butyl methyl ether, or ketones such as acetone or butanone, or amides such as dimethylformamide or hexamethyl-phosphoramide, or hydrocarbons such as hexane, benzene, dichlorobenzene, xylene or toluene, or dimethyl sulphoxide, acetonitrile, ethyl acetate, or halogenohydrocarbons such as methylene chloride, chloroform or carbon tetrachloride, or pyridine, picoline or N-methylpiperidine. Mixtures of the solvents mentioned can also be used.

Suitable bases, depending on the individual process steps, are the customary inorganic or organic bases. These preferably include alkali metal hydroxides such as, for example, sodium or potassium hydroxide, or alkali metal carbonates such as sodium or potassium carbonate, or alkali metal alkoxides such as, for example, sodium or potassium methoxide, or sodium or potassium ethoxide, or organic amines such as ethyldiisopropylamine, triethylamine, picoline, pyridine or N-methylpiperidine, or amides such as sodium amide or lithium diisopropylamide, or lithium N-silylalkylamides, such as, for example, lithium N-(bis) triphenylsilylamide or lithium alkyls such as n-butyllithium.

The base is employed in an amount from 1 mol to 10 mol, preferably from 1 mol to 3 mol, in each case relative to 1 mol of the compounds of the general formulae (II) and (IV).

All reactions are in general carried out at normal, elevated or reduced pressure (e.g. 0.5 to 5 bar). In general, the reactions are carried out at normal pressure.

The compounds of the general formulae (III) and (V) are known per se or can be prepared by customary methods.

The compounds of the general formula (II) are known in some cases and can be prepared by converting compounds of the general formula (VI)

$$\text{(VI)}$$

in which

A has the meaning indicated above, by reaction with $(C_1-C_4)$-alkyl- or phenylsulphonyl chlorides in inert solvents and in the presence of a base into the corresponding compounds of the general formula (IV)

$$\text{(IV)}$$

in which

A and $R^{37}$ have the meaning indicated above, then with sodium azide in inert solvents preparing the azides of the general formula (VII)

$$\text{(VII)}$$

in which

A has the meaning indicated above, in a further step converting into the amines by reaction with $(C_1-C_4-O)_3$—P or $PPh_3$, preferably $(CH_3O)_3P$ in inert solvents and with acids.

Depending on the individual process steps, suitable solvents are the customary solvents which do not change under the reaction conditions. These preferably include alcohols such as methanol, ethanol, propanol or isopropanol, or ethers such as diethyl ether, dioxane, 1,2-dimethoxyethane, tetrahydrofuran, glycol dimethyl ether or tert-butyl methyl ether, or ketones such as acetone or butanone, or amides such as dimethylformamide or hexamethyl-phosphoramide, or hydrocarbons such as hexane, benzene, dichlorobenzene, xylene or toluene, or dimethyl sulphoxide, acetonitrile, ethyl acetate, or halogenohydrocarbons such as methylene chloride, chloroform or carbon tetrachloride, or pyridine, picoline or N-methylpiperidine. Mixtures of the solvents mentioned can also be used.

Depending on the individual process steps, suitable bases are the customary inorganic or organic bases. These preferably include alkali metal hydroxides such as, for example, sodium or potassium hydroxide, or alkali metal carbonates such as sodium or potassium carbonate, or alkali metal alkoxides such as, for example, sodium or potassium methoxide, or sodium or potassium ethoxide, or organic amines such as ethyldiisopropylamine, triethylamine, picoline, pyridine or N-methylpiperidine, or amides such as sodium amide or lithiumdiisopropylamide, or lithium N-silylalkylamides, such as, for example, lithium N-(bis)triphenylsilylamide or lithium alkyls such as n-butyllithium.

The base is employed in an amount from 1 mol to 10 mol, preferably from 1 mol to 3 mol, relative to 1 mol of the compounds of the general formula (VI).

All reactions are in general carried out at normal, elevated or reduced pressure (e.g. 0.5 to 5 bar). In general, the reactions are carried out at normal pressure.

The reduction of the azides is carried out using $(CH_3O)_3P$ and hydrochloric acid.

The reduction is in general carried out in a temperature range from $-50°$ C. up to the respective boiling point of the solvent, preferably from $-20°$ C. to $+90°$ C.

Suitable solvents in this context are all inert organic solvents which do not change under the reaction conditions. These preferably include alcohols such as methanol, ethanol, propanol or isopropanol, or ethers such as diethyl ether, dioxane, tetrahydrofuran, glycol dimethyl ether, or diethylene glycol dimethyl ether or amides such as hexamethylphosphoramide or dimethylformamide, or acetic acid. It is also possible to use mixtures of the solvents mentioned.

The compounds of the general formulae (IV) and (VII) are new and can be prepared as described above.

The compounds of the general formula (VI) are new in some cases and can be prepared by

[D] reacting compounds of the general formula (VIII) or (IX)

A—N=C=O           (VIII)

or

A—CO—N$_3$         (IX)

in which

A has the meanings indicated above, with lithium bromide/$(C_4H_9)_3P(O)$ and epoxides of the general formula (X)

(X)

in which

Q represents $C_1$–$C_6$-acyloxy, in inert solvents, if appropriate in the presence of a base, liberating the hydroxyl function by means of a typical ester hydrolysis or by means of a typical transesterification, or

[E] reacting compounds of the general formula (XI)

A—NH—CO$_2$—X       (XI)

in which

A has the meaning indicated above and

X represents a typical protective group, preferably benzyl, in inert solvents and in the presence of a base, for example lithium alkyls or lithium N-alkyl- or lithium N-silylalkylamides, preferably n-butyllithium, with epoxides of the general formula (X), or first converting compounds of the general formula (IX) by elimination of nitrogen in alcohols into the compounds of the general formula (XIa)

A—NH—CO$_2$—Y       (XIa)

in which

A has the meaning indicated above and

Y represents a straight-chain or branched $C_2$–$C_6$-alkyl, preferably n-butyl, and in a second step as described under [D] reacting in inert solvents and in the presence of a base, preferably lithium N-alkyl- or N-silylalkylamides or n-butyllithium and epoxides of the general formula (X), or

[F] reacting compounds of the general formula (XII)

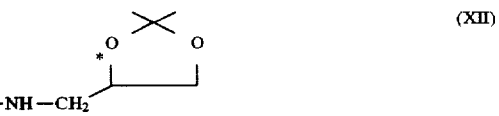

(XII)

in which

A has the meaning indicated above, either directly with acids and diethyl carbonate, or first by reaction of the compounds of the general formula (XII) with acids preparing the compounds of the general formula (XIII)

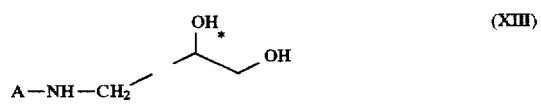

(XIII)

in which

A has the meaning indicated above, and then cyclizing in the presence of an auxiliary in inert solvents.

Depending on the individual process steps, suitable solvents are the customary solvents which do not change under the reaction conditions. These preferably include alcohols such as methanol, ethanol, propanol or isopropanol, or ethers such as diethyl ether, dioxane, 1,2-dimethoxyethane, tetrahydrofuran, glycol dimethyl ether or tert-butyl methyl ether, or ketones such as acetone or butanone, or amides such as dimethylformamide or hexamethyl-phosphoramide, or hydrocarbons such as hexane, benzene, dichlorobenzene, xylene or toluene, or dimethyl sulphoxide, acetonitrile, ethyl acetate, or halogenohydrocarbons such as methylene chloride, chloroform or carbon tetrachloride, or pyridine, picoline or N-methylpiperidine. Mixtures of the solvents mentioned can also be used.

Depending on the individual process steps, suitable bases are the customary inorganic or organic bases. These preferably include alkali metal hydroxides such as, for example, sodium or potassium hydroxide, or alkali metal carbonates such as sodium or potassium carbonate, or alkali metal alkoxides such as, for example, sodium or potassium methoxide, or sodium or potassium ethoxide, or organic amines such as ethyl diisopropylamine, triethylamine, picoline, pyridine or N-methylpiperidine, or amides such as sodium amide or lithiumdiisopropylamide, or lithium N-silylalkylamides, such as, for example, lithium N-(bis)triphenylsilylamide or lithium alkyls such as n-butyllithium.

The base is employed in an amount from 1 mol to 10 mol, preferably from 1 mol to 3 mol, relative to 1 mol of the compounds of the general formulae (X) and (XI).

All reactions are in general carried out at normal, elevated or reduced pressure (e.g. 0.5 to 5 bar). In general, the reactions are carried out at normal pressure.

Process [D] is preferably carried out in xylene or dichlorobenzene, if appropriate in the presence of triethylamine, under reflux.

The base-catalysed transesterification is carried out using one of the abovementioned alcohols, preferably methanol, in a temperature range from −10° C. to +40° C., preferably at room temperature.

Suitable bases are in general sodium hydrogen carbonate, sodium methoxide, hydrazine hydrate, potassium carbonate or caesium carbonate. Caesium carbonate is preferred.

Process |E| is carried out in one of the abovementioned ethers using lithium alkyl compounds or lithium N-silylamides, such as, for example, n-butyllithium, lithium diisopropylamide or lithium bistrimethylsilylamide, preferably in tetrahydrofuran and lithium bis-trimethylsilylamide or n-butyllithium, in a temperature range from −100° C. to +20° C., preferably from −75° C. to −40° C.

For process |F| preferably the abovementioned alcohols are suitable for the 1st step, in the case of subsequent cyclization, tetrahydrofuran.

Suitable bases for the cyclization are preferably the abovementioned lithium N-silylalkyl compounds or n-butyllithium. n-Butyllithium is particularly preferred.

The first reaction step is carried out at the boiling point of the corresponding alcohol; the cyclization in a temperature range from −70° C. to room temperature.

The cyclization |F| is carried out in the presence of an auxiliary and/or presence of an acid.

Suitable acids are in general inorganic acids such as, for example, hydrochloric acid or sulphuric acid, or organic carboxylic acids having 1–6 C. atoms, optionally substituted by fluorine, chlorine and/or bromine, such as, for example, acetic acid, trifluoroacetic acid, trichloroacetic acid or propionic acid, or sulphonic acids having $C_1$–$C_4$-alkyl radicals or aryl radicals, such as, for example, methanesulphonic acid, ethanesulphonic acid, benzenesulphonic acid or toluenesulphonic acid. Hydrochloric acid is particularly preferred.

The acid is employed in an amount from 1 mol to 10 mol, preferably from 1 mol to 2 mol, relative to 1 mol of the compounds of the general formula (XII).

Suitable auxiliaries are the customary reagents such as phosgene, carbonyldiimidazole or diethyl carbonate or trichloromethyl chloroformate. Carbonyldiimidazole, diethyl carbonate and trichloromethyl chloroformate are preferred.

Suitable solvents are the abovementioned halogenohydrocarbons. Methylene chloride is preferred.

The compounds of the general formula (IX) are known or can be prepared by customary methods.

The compounds of the general formula (XIII) are in the main new and can be prepared, for example, as described above.

The compounds of the general formula (VIII) are known in some cases or are new and can then be prepared, for example, by reacting the corresponding amines with trichloroethyl chloroformate in one of the abovementioned solvents, preferably xylene at reflux temperature.

The compounds of the general formula (IX) are in some cases known or are new and can then be prepared, for example, by starting from the corresponding carboxylic acids either reacting with isobutyl chloroformate/acetone, sodium azide/water or with diphenylphosphoryl azide/ tetrahydrofuran or with xylene or methylene chloride in the presence of one of the bases indicated above, preferably triethylamine, at −10° C. to room temperature.

The compounds of the general formulae (XI) and (XIa) are known in some cases or are new and can be prepared either by elimination of nitrogen from the corresponding carboxylic acid azides and reaction with the appropriate alcohols or by reaction of the corresponding amines with chloroformic acid esters, preferably benzyl chloroformate, in one of the abovementioned solvents, preferably tetrahydrofuran or dioxane, in a temperature range from −10° C. to 200° C., preferably from 0° C. to 150° C.

The minimum inhibitory concentrations (MIC) were determined by serial dilution methods on Iso-Sensitest Agar (Oxoid). For each test substance, a number of agar plates were prepared which, with an in each case doubled dilution, contained decreasing concentrations of the active compound. The agar plates were inoculated with the multipoint inoculator (Denley). For inoculation, overnight cultures of the caustive organisms were used which had previously been diluted such that each inoculation point contained about $10^4$ colony-forming particles. The inoculated agar plates were incubated at 37° C., and the microorganism growth was read off after about 20 hours. The MIC value (μg/ml) indicates the lowest active compound concentration at which no growth could be detected using the naked eye.

| | | | MIC values (μg/ml): | | | | |
|---|---|---|---|---|---|---|---|
| Ex. No. | Staph. 133 | Staph. 48N | Staph. 25701 | Staph. 9TV | E. coli Neu- mann | Klebs. 57 USA | Psdm. Bonn |
| 11 | 0.5 | 0.5 | 0.25 | 0.25 | >64 | >64 | >64 |
| 12 | 1 | 1 | 1 | 0.5 | >64 | >64 | >64 |
| 13 | 0.25 | 0.25 | 0.25 | ≦0.125 | >64 | >64 | >64 |
| 14 | 1 | 1 | 1 | 0.5 | >64 | >64 | >64 |
| 15 | 0.25 | 0.5 | 0.25 | ≦0.125 | >64 | >64 | >64 |
| 20 | 0.25 | 0.25 | 0.25 | ≦0.125 | 64 | >64 | >64 |
| 23 | 0.25 | 0.5 | 0.5 | 0.25 | >64 | >64 | >64 |
| 26 | <0.125 | 0.25 | 0.25 | ≦0.125 | >64 | >64 | >64 |
| 42 | <0.125 | >0.125 | >0.125 | ≦0.125 | 64 | 64 | >64 |
| 43 | 0.5 | 0.5 | 0.5 | 0.5 | >64 | >64 | >64 |

For rapidly growing mycobacteria the MIC determination was carried out following the broth microdilution method described by Swenson [cf. J. M. Swenson, C. Thornberry, U. A. Silcox, Rapidly growing mycobacteria. Testing of susceptibility to 34 antimicrobial agents by broth microdilution. Antimicrobial Agents and Chemotherapy Vol. 22, 186–192 (1982)]. A deviation from this was the brain-heart extract medium treated with 0.1% by volume of Tween 80.

The mycobacterial strains used were obtained from the DSM (German Collection of Microorganisms, Brunswick). They were incubated at 37° C. in a humid chamber.

The MIC values were read off after 2–4 days when the preparation-free controls had become turbid due to growth. The MIC value is defined as the lowest preparation concentration which completely inhibits macroscopically visible growth.

| MIC values: *Mycobacterium smegmatis* | | |
|---|---|---|
| Strain: | DSM 43061 | DSM 43078 |
| Inoculum [/ml] | 2.20E + 04 | 4.20E + 04 |
| Ex. No. | | |
| 12 | 8 | 4 |
| 13 | 2 | 1 |
| 14 | 8 | 4 |
| 15 | 1 | 0.5 |
| 20 | 0.25 | 0.25 |
| Isoniazide | 4 | 2 |
| Strepto-mycin | 4 | 4 |

MIC determination with Mycoplasma pneumoniae

Mycoplasma pneumoniae strain PI 1428 was cultured under anaerobic conditions in PPLO medium, to which 1% glucose, 2.5% yeast extract, 20% horse serum (donor horse serum) and 0.002% Phenol Red were added. MIC determinations were carried out following the serial microdilution method in liquid medium described by ter Laak and coworkers (E. A. ter Laak, A. Pijpers, J. H. Noordergraaf, E. Schoevers, J. H. M. Verheijden: Comparison of Methods for in vitro Testing of Susceptibility of Porcine Mycoplasma Species to Antimicrobial Agents; Antimicrobial Agents and Chemotherapy, Vol. 35, 228–233 (1991)). At the time of the start of the colour change of the medium of the preparation-free control from red to yellow, 10% by volume of Alamar Blue was added. The incubation at 37° C. was continued for about 10 hours and the MIC defined as the value at which the medium having the smallest preparation concentration remained unchanged blue.

| Ex. No. | MIC (µg/ml) |
|---------|-------------|
| 12      | 2           |
| 13      | 2           |
| 14      | 8           |
| 23      | 4           |

The compounds of the general formula (I) according to the invention have a broad antibacterial spectrum combined with low toxicity, especially against gram-positive bacteria and mycobacteria, Haemophilus influenzae, anaerobic microorganisms for rapidly-growing mycobacteria. These properties make possible their use as chemotherapeutic active compounds in human and veterinary medicine.

The compounds according to the invention are particularly effective against bacteria and bacteria-like microorganisms such as mycoplasma. They are therefore particularly highly suitable for the prophylaxis and chemotherapy of local and systemic infections in human and veterinary medicine which are caused by such pathogens.

The present invention includes pharmaceutical preparations which, besides non-toxic, inert pharmaceutically suitable excipients, contain one or more compounds according to the invention or which consist of one or more active compounds according to the invention, and processes for the production of these preparations.

The active compound or compounds can optionally be present in one or more of the excipients indicated above, alternatively in microencapsulated form.

The therapeutically active compounds should be present in the abovementioned pharmaceutical preparations in a concentration of approximately 0.1 to 99.5, preferably of approximately 0.5 to 95, % by weight of the total mixture.

Apart from the compounds according to the invention, the abovementioned pharmaceutical preparations can also contain further pharmaceutical active compounds.

In general, it has proved advantageous both in human and in veterinary medicine to administer the active compound or compounds according to the invention in total amounts from approximately 0.5 to approximately 500, preferably 5 to 100, mg/kg of body weight every 24 hours, if appropriate in the form of several individual doses, to achieve the desired results. An individual dose contains the active compound or compounds according to the invention preferably in amounts from approximately 1 to approximately 80, in particular 3 to 30, mg/kg of body weight.

For the purpose of extending the spectrum of action and in order to achieve an increase in action, the compounds according to the invention can also be combined with other antibiotics.

Appendix to the Experimental Section
List of the eluent mixtures used for chromatography:
I Dichloromethane:methanol
II Toluene:ethyl acetate
III Acetonitrile:water
IV Ethyl acetate
V Petroleum ether:ethyl acetate
VI $CH_2Cl_2$:MeOH:$NH_{3(aq)}$
VII $CH_2Cl_2$:MeOH
Abbreviations:
Z Benzyloxycarbonyl
Boc tert-Butoxycarbonyl
DMF Dimethylformamide
Ph Phenyl
Me Methyl
THF Tetrahydrofuran
CDI Carbonyldiimidazole
DCE Dichloroethane If not stated otherwise, the examples mentioned below can be prepared according to or in analogy to the instructions in EP 694 543, EP 693 491, EP 694 544, EP 697 412 and EP 738 726.

Starting Compounds

EXAMPLE I

5-Bromo-2-isocyanato-pyridine Hydrochloride

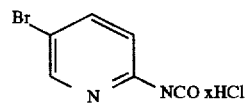

78.0 ml (0.64 mol) of trichloroethyl chloroformate are added dropwise at boiling heat to a stirred solution of 100 g (0.58 mol) of 2-amino-5-bromopyridine in 400 ml of 1,2-dichloroethane. After the addition the mixture is refluxed for 2 h, then it may be cooled to room temperature. The resulting precipitate is removed by filtration, washed well with 100 ml of 1,2-dichloroethane and dried over sodium hydroxide in a high vacuum. 98.3 g (72%) of the title compound are obtained as a yellow solid.

M.p.: 248°–254° C. (dec.) $R_f$=0.23 (ethyl acetate) MS (EI) m/z=198 (M)$^+$

EXAMPLE II (5R)-3-(5-Bromo-pyridin-2-yl)-5-butyryloxy-methyl-oxazolidin-2-one

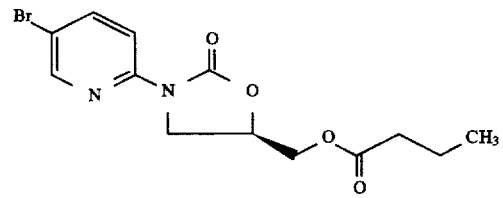

A suspension of 2.17 g (25 mmol) of lithium bromide and 5.46 g (25 mmol) of tributylphosphine oxide in 73 ml of xylene is boiled in a water separator for 1 h. A mixture of 58.5 ml (0.42 mol) of triethylamine and 66.6 g (0.42 mol) of (R)-glycidyl butyrate is added dropwise to this at boiling heat. At the same time, 98.2 g (0.42 mol) of the compound from Example I are added in portions in the course of 20 min. After addition is complete, the mixture is stirred under reflux for 1 h. It is allowed to cool to room temperature and the solvent is evaporated in vacuo. After chromatography of the residue on 1 kg of silica gel (toluene:ethyl acetate 95:5), 37.9 g (26%) of the title compound are obtained as an oil.

$R_f$=0.43 (toluene:ethyl acetate 4:1) MS (FAB) m/z=343 (M+H)$^+$ $^1$H-NMR (250 MHz, D$_6$-DMSO): δ=0.81 (t, J=7 Hz, 3H, CH$_3$CH$_2$); 1.5 (m, 2H, CH$_3$CH$_2$CH$_2$CO); 2.29 (t, J=7 Hz, 2H, CH$_3$CH$_2$CH$_2$CO); 3.91 (dd, J=7 Hz, 10 Hz, 1H, H-4 trans); 4.25 (dd, J=9 Hz, 10 Hz, 1H, H-4 cis); 4.36 (m, 2H, CH$_2$O); 4.97 (m, 1H, H-5); 8.08 (d, J=1 Hz, 2H, pyridyl H-3,4); 8.50 (d, J=1 Hz, pyridyl H-6).

EXAMPLE III (5R)-3-(5-Bromo-pyridin-2-yl)-5-hydroxymethyl-oxazolidin-2-one

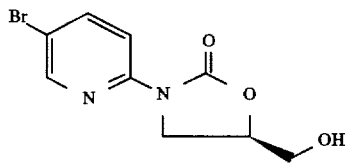

A solution of 19.6 g (57.3 mmol) of the compound from Example II in 125 ml of anhydrous methanol is treated with 185 mg (0.57 mmol) of caesium carbonate and stirred at room temperature for 5 h. The solvent is evaporated in vacuo and the residue is stirred with 30 ml of ether. The precipitate is removed by filtration, washed with 25 ml of water and 5 ml of ether and dried in a high vacuum. 10.73 g (69%) of the title compound are obtained as pale crystals.

M.p.: 0.09 (toluene:ethyl acetate 4:1) MS (DCI, NH$_3$) m/z=273 (M+H)$^+$ $^1$H-NMR (200 MHz, CD$_3$OD) δ=3.68 (d, J=5.9 Hz, 1 H, CH$_2$O); 3.87 (dd, J=4, 9 Hz, 1H, CH$_2$O); 4.06 (dd, J=7, 10 Hz, 1H, H-4 trans); 4.26 (dd, J=9, 10 Hz, 1H, H-4 cis); 4.75 (m, 1H, H-5); 7.92 (dd, J=1.5 Hz, 10 Hz, 1H, pyridyl H-3); 8.12 (d, J=10 Hz, 1H, pyridyl H-4); 8.40 (d, J=1.5 Hz, 1H, pyridyl H-6).

EXAMPLE IV 5-(2-Pyridyl)-thiophene-2-carboxylic Acid Azide

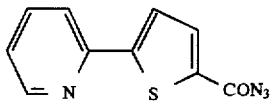

20 g (97.45 mmol) of 5-(2-pyridyl)-thiophene-2-carboxylic acid are dissolved in 200 ml of acetone, and the solution is treated with 15.94 ml (115 mmol) of Et$_3$N and cooled to 0° C. A solution of 14.85 ml (115 mmol) of isobutyl chloroformate in 88 ml of acetone is slowly added dropwise with stirring to the reaction solution thus obtained. After 1 h at 0° C., a solution of 9.5 g (146 mmol) of sodium azide in 44 ml of water is added dropwise, and the mixture is stirred at 0° C. for 1 h and allowed to come to room temperature. The reaction mixture is tipped onto ice water and the precipitate is filtered off with suction and reacted further as it is.

Yield: 21 g of water-moist powder.

EXAMPLE V 5-(2-Pyridyl)-butyloxycarbonylamino-thiophene

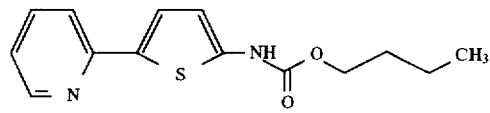

21 g of the compound from Example IV are introduced in portions into 400 ml of boiling n-butanol. After evolution of gas is complete, the mixture is stirred under reflux for 15 min. After cooling to room temperature it is concentrated, and the residue is stirred with ether, filtered off with suction and dried at 50° C. in a recirculating air cabinet.

Yield: 18.8 g (75% of theory)

$^1$H-NMR (200 MHz, D$_6$-DMSO): δ=10.8 (s, 1H); 8.45 (d, J=5 Hz, 1H); 7.68–7.85 (m, 2H); 7.5 (d, J=5 Hz, 1H); 7.1–7.2 (m, 1H); 6.57 (d, J=5 Hz, 1H); 4.14 (t, J=7 Hz, 2H); 1.62 (q, J=7 Hz, 2H); 1.39 (h, J=7 Hz, 2H); 0.92 (t, J=7 Hz, 3H).

EXAMPLE VI (5R)-3-(5-(2-Pyridyl)-thien-2-yl)-5-hydroxymethyl-oxazolidin-2-one

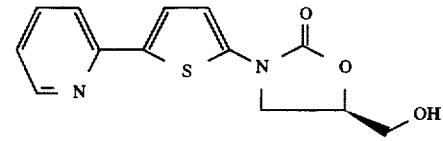

18.8 g (68 mmol) of the compound from Example V are dissolved in 190 ml of absolute THF, and the solution is treated with 10 mg of 1,10-phenanthroline hydrate and cooled to –70° C. About 27 ml of 2.5 N n-butyllithium solution in hexane are then slowly added dropwise until the colour changes to red. 9.6 ml (68 mmol) of (R)-glycidyl butyrate are then added dropwise. The mixture is allowed to come to room temperature and is treated with saturated ammonium chloride solution, the organic phase is separated off and the aqueous phase is extracted twice with methylene chloride. The combined organic phases are dried (Na$_2$SO$_4$) and concentrated. The residue is stirred with ether and filtered off with suction.

Yield: 15.3 g (81.5% of theory) $R_f$=0.06 (CH$_2$Cl$_2$:CH$_3$OH=100:3) M.p.: 191° C.

$^1$H-NMR (200 MHz, D$_6$-DMSO): δ=8.45 (d, J=5 Hz, 1H); 7.7–7.9 (m, 2H); 7.6 (d, J=5 Hz, 1H); 7.15–7.25 (m, 1H); 6.58 (d, J=5 Hz, 1H); 5.28 (t, J=7 Hz, 1H); 4.77–4.9 (m, 1H); 4.13 (dd, J=10 Hz, 9 Hz, 1H); 3.86 (dd, J=10 Hz, 6 Hz, 1H); 3.55–3.78 (m, 2H).

EXAMPLE VII 6-(Benzyloxycarbonylamino)-3-methyl-2-benzothiazolinone

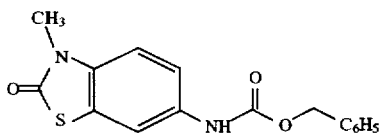

1.76 g (8.12 mmol) of 6-amino-3-methyl-2(3H-benzothiazolone hydrochloride in 17 ml of water, 14 ml of THF and 17 ml of satd. NaHCO₃ solution are treated dropwise at 0° C. with 1.3 ml (9.10 mmol) of benzyl chloro-formate. After 1 h, 120 ml of water are added, the THF is stripped off in vacuo, and the precipitate is filtered off with suction, washed three times with water and twice with petroleum ether and dried at 60° C.

Yield: 2.44 g (96%) M.p.: 183° C. $R_f$ (II, 7:3)=0.39

¹H-NMR (|D₆|DMSO): δ=7.77 (d, J=1 Hz, 1H, benzothiazolinone 7-H); 7.23–7.45 (m, 6H, Ph), 7.22 (d, J=6 Hz, 1H, benzothiazolinone 4-H); 5.15 (s, 2H); 3.38 (s, 3H-CH₃).

EXAMPLE VIII (5R)-3-[3-(Methyl-2-benzothiazolion-6-yl]-5-(hydroxymethyl)-oxazolidin-2-one

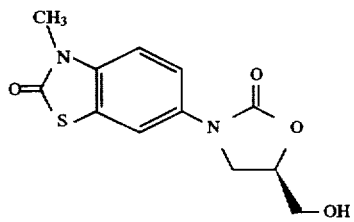

Method A 26.76 g (85.12 mmol) of the compound from Example VII are dissolved in 400 ml of THF, and the solution is treated with 10 mg of 1.10-phenanthroline hydrate and cooled to −70° C. About 34 ml of 2.5N n-butyllithium solution in hexane are then slowly added dropwise until the colour changes to red. 12 ml (85.12 mmol) of (R)-glycidyl butyrate are then added dropwise. The mixture is allowed to come to RT and is treated with saturated ammonium chloride solution, and the THF is stripped off in vacuo. The resultant precipitate is filtered off with suction, washed with water and ether and dried in a high vacuum.

Yield: 17.93 g (75%) M.p.: 166° C. $R_f$ (II, 1:1)=0.09 MS (EI): m/z=280 (M)⁺

¹H-NMR (|D₆|DMSO): δ=7.80 (d, J=1 Hz, 1H, benzothiazolinone 7-H); 7.60 (dd, J=6, J=1 Hz, 1H, benzothiazolinone 5-H); 7.32 (d, J=6 Hz, 1H, benzothiazolinone 4-H); 5.23 (t, J=6 Hz, 1H, OH); 4.62–4.80 (m, 1H, 5-H); 4.10 (t, J=9 Hz, 1H, 4-H); 3.85 (dd, J=9, J=5 Hz, 1H, 4-H); 3.48–3.75 (m, 2H, CH₂O); 3.40 (s, 3H, CH₃).

Method B 9.3 g (0.03 mol) of the compound from Example VII are dissolved in 150 ml of THF and the solution is cooled to −70° C. 4 ml (0.01 mol) of 2.5M n-butyllithium solution in hexane are then added dropwise. 8 ml (0.02 mol) of n-butyllithium and 4.23 ml (0.03 mol) of (R)-glycidyl butyrate are then slowly added dropwise simultaneously. The mixture is allowed to come to room temperature and is stirred for 3 hours. Working-up is carried out as described for method A. Yield: 6 g (72%).

The compounds listed in Table I are prepared analogously to the procedures of Examples I to VIII:

TABLE I

| Ex. No. | A | Mp (°C.) | $R_f$/ Eluent (ratio) | Yield (% of theory) |
|---|---|---|---|---|
| IX | benzothiophene | 162 | — | 63 |
| X | pyridyl-thiophene | 209 dec. | — | 61 |
| XI | pyridyl-thiophene | 185 | — | 71 |

TABLE I-continued
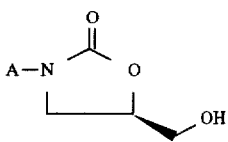
| Ex. No. | A | Mp (°C.) | $R_f$/ Eluent (ratio) | Yield (% of theory) |
|---|---|---|---|---|
| XII | 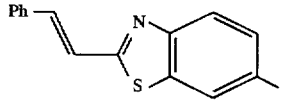 | 188 | 0.52, I (9:1) | 76 |
| XIII | 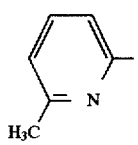 | 144 | 0.32, I (95:5) | 78 |
| XIV | 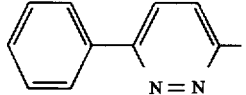 | 158 | 0.29, II (1:1) | 28 |
| XV | 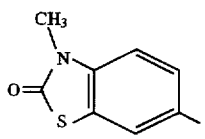 | 166 | 0.09, II (1:1) | 82 |
| XVI | 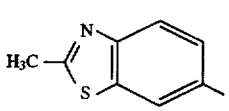 | — | 0.05, II (1:1) | 57 |
| XVI | 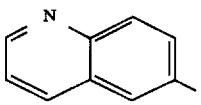 | 132 | — | 79 |
| XVII | 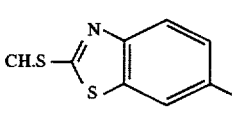 | 165 | 0.1, V (1:4) | 45 |
| XVIII | 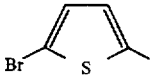 | 156 | 0.24, V (4:1) | 67 |
| XIX | 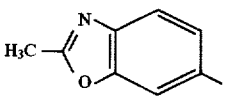 | 109 | — | 24 |
| XX | 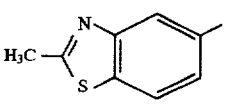 | — | 0.47, II (1:1) | 68 |
| XXI |  | — | 0.05, II (1:1) | 57 |

TABLE I-continued

| Ex. No. | A | Mp (°C.) | R_f/Eluent (ratio) | Yield (% of theory) |
|---|---|---|---|---|
| XXII | 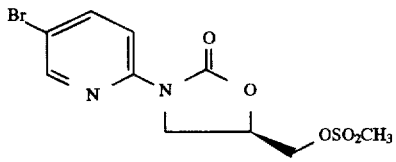 | 200 dec. | — | 98 |

EXAMPLE XXIII (5R)-3-(5-Bromo-pyridin-2-yl)-5-methanesulphonyloxy-methyl-oxazolidin-2-one

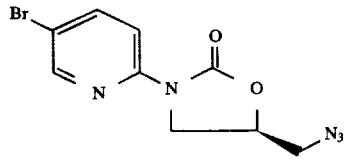

A stirred solution, cooled to 0° C., of 10.5 g (38.44 mmol) of the compound from Example III and 6.40 ml (46.14 mmol) of triethylamine in 36 ml of anhydrous dichloromethane is slowly treated with 3.27 ml (42.28 mmol) of methanesulphonyl chloride. The mixture is stirred at 0°–5° C. for 10 min. and stirred into 50 ml of ice-water. The organic phase is separated off, washed with 20 ml of saturated $NaHCO_3$ solution and 20 ml of ice-water and dried over $MgSO_4$. The solvent is evaporated in vacuo and the residue is stirred with 50 ml of ether, filtered off with suction and dried in a high vacuum. 12.8 g (95%) of the title compound are obtained as colourless crystals.

M.p.: 138°–138.5° C. $R_f=0.65$ (dichloromethane:methanol 95:5) MS (DCI, $NH_3$) m/z=351 $(M+H)^+$ $^1$H-NMR (250 MHz, $D_6$-DMSO) δ=3.25 (s, 3H, $OSO_2CH_3$); 3.91 (dd, J=7, 10 Hz, 1H, H-4 trans); 4.27 (dd, J=10, 10 Hz, 1H, H-4 cis); 4.52 (m, 2H, $CH_2O$); 5.02 (m, 1H, H-5); 8.09 (s, 2H, pyridyl H-3,4); 8.52 (s, 1H, pyridyl H-6).

EXAMPLE XXIV (5R)-3-(5-Bromo-pyridin-2-yl)-5-azidomethyl-oxazolidin-2-one

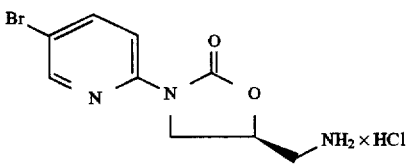

A stirred solution of 12.5 g (35.6 mmol) of the compound from Example XXIII in 48 ml of anhydrous DMF is treated with 3.01 g (46.28 mmol) of sodium azide and stirred at 70° C. for 3 h. It is allowed to cool to room temperature and stirred into 100 ml of ice-water. The resultant precipitate is removed by filtration, washed with 50 ml of water and 20 ml of petroleum ether and dried in air. 10.1 g (95%) of the title compound are obtained as pale crystals.

M.p.: 64°–67° C. $R_f=0.63$ (toluene:ethyl acetate 2:3) MS (DCI, $NH_3$) m/z=298 $(M+H)^+$ $^1$H-NMR (250 MHz, $D_6$-DMSO) δ=3.73 (m, 2H, $CH_2N_3$); 3.87 (dd, J=6, 8 Hz, 1H, H-4 trans); 4.22 (dd, J=8, 8 Hz, 1H, H-4 cis); 4.92 (m, 1H, H-5); 8.08 (s, 2H, pyridyl H-3, 4); 8.51 (s, 1H, pyridyl H-6).

EXAMPLE XXV (5S)-3-(5-Bromo-pyridin-2-yl)-5-aminomethyl-oxazolidin-2-one Hydrochloride A stirred solution of 10.1 g (33.9 mmol) of the compound from Example XXIV in 16.5 ml of 1,2-dimethoxyethane is warmed to 50° C. 4.68 ml (4.70 mmol) of trimethyl phosphite are slowly added dropwise (evolution of gas) and stirred at 90° C. for 2 h after addition is complete. 6.6 ml of 6 N HCl are then added dropwise and the mixture is stirred at 90° C. for a further 2 h. It is allowed to cool to room temperature, and the precipitate is removed by filtration, washed with 2×10 ml of 1,2-dimethoxyethane and dried in a high vacuum over NaOH. 8.9 g (85%) of the title compound are obtained as colourless crystals.

M.p.: 260°–262° C. $R_f=0.53$ (acetonitrile water 4:1) MS (EI) m/z =271 $(M)^+$ $^1$H-NMR (250 MHz, $D_6$-DMSO) δ=3.28 (m, 2H, $CH_2NH_2$); 3.93 (dd, J 7, 9 Hz, 1H, H-4 trans); 4.28 (dd, J=9, 9 Hz, 1H, H-4 cis); 5.00 (m, 1H, H-5); 8.05 (s, 2H, pyridyl H-3, 4); 8.5 (m, 3H, $NH_2$, pyridyl H-6).

EXAMPLE XXVI (5S)-3-(5-Bromo-pyridin-2-yl)-5-((tert-butyloxy)carbonyl)aminomethyl-oxazolidin-2-one

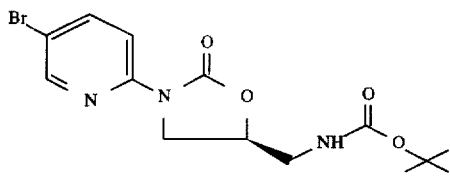

4.7 g (15 mmol) of the compound from Example XXV are suspended in 100 ml of CH₂Cl₂. 2.2 ml (16 mmol) of triethylamine are then added, a solution resulting. This is cooled to 0° C. 3.5 g (16 mmol) of Boc anhydride are then added such that the temperature does not exceed +5° C. and the mixture is stirred overnight at room temperature. The organic phase is washed with satd. NaCl solution, dried over MgSO₄ and concentrated. 5.4 g (97% of theory) of the product are obtained as a white solid.

M.p.: 184° C. $R_f$ value (petroleum ether:ethyl acetate=10:4)=0.30

EXAMPLE XXVII ((5S)-3-(5-[3-Pyridyl]-pyridin-2-yl)-5-(tert-butyloxy)carbonyl)aminomethyl-oxazolidin-2-one

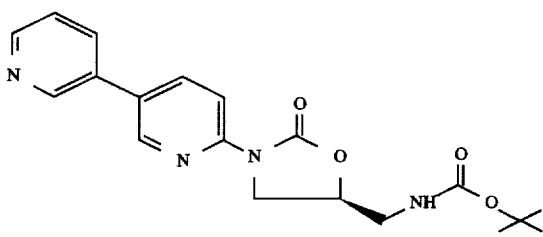

5.3 g (14.24 mmol) of the compound from Example XXVI and 2.81 g of diethyl-(3-pyridyl)-borane in 100 ml of abs. THF are initially introduced under argon. A solution of 0.5 g (0.43 mmol) of [(PPh₃)₄Pd] in 90 ml of THF and 4.9 ml (9.83 mmol) of 2M sodium carbonate solution is added. The mixture is stirred under reflux for 5 days. After cooling to RT, 10 g of kieselguhr are added and the mixture is concentrated. The residue is applied to a column packed with silica gel and eluted using ethyl acetate. 4 g (76% of theory) of the title compound are obtained M.p.: 163° C. $R_f$ value=0.36 (CH₂Cl₂:MeOH=100:5)

EXAMPLE XXVIII (5S)-3-(5-[3-Pyridyl]-pyridin-2-yl)-5-aminomethyl-oxazolidin-2-one Trihydrochloride 3.8 g (10.3 mmol) of the compound from Example XXVII are suspended in 25 ml of dioxane. 32.1 ml of a 4M HCl solution in dioxane are added and the mixture is stirred at room temperature overnight. It is concentrated and the residue is washed by stirring with ether. The solid is then filtered off with suction through a frit and washed with ether. It is dried in a high vacuum and 3.7 g (95% of theory) of the title compound are obtained.

M.p.: >250° C. MS (EI): 271 (M)⁺, 172

¹H-NMR (200 MHz, DMSO-d₆): δ=9.35 (sb, 1H); 8.93 (m, 3H); 8.6 (broad, 3H); 8.42 (dd, J=9, J=3, 1H); 8.24 (d, J=9, 1H); 8.11(dd, J=7.5, J=6.5, 1H); 6.7–5.3 (broad, 2H); 5.06 (m, 1H); 4.38 (tr, J=10, 1H); 4.03 (dd, J=10, J=7.5, 1H); 3.29 (m, 2H).

The compounds listed in Table II are prepared analogously to the procedures of Examples XXIII to XXVIII:

TABLE II

| Ex. No. | A | Mp (°C.) | $R_f$/ Eluent (ratio) | Yield (% of theory) |
|---|---|---|---|---|
| XXIX | (pyridyl-thienyl) | — | — | 95 |
| XXX | (benzothienyl) | — | — | 87 |

TABLE II-continued

A—N(C=O)O [ring with NH₂·xHCl substituent]

| Ex. No. | A | Mp (°C.) | R_f / Eluent (ratio) | Yield (% of theory) |
|---|---|---|---|---|
| XXXI | pyridyl-thienyl | — | — | 94 |
| XXXII | pyridyl-thienyl | — | — | 94 |
| XXXIII | Ph-CH=CH-benzothiazolyl | 303 | 0.19, III (9:1) | 94 |
| XXXIV | methylpyridyl | — | 0.21, III (9:1) | 75 |
| XXXV | phenyl-pyridazinyl | 273 | 0.24, III (4:1) | 75 |
| XXXVI | 3-methyl-2-oxo-benzothiazolyl | 259 dec | 0.09, III (9:1) | 75 |
| XXXVII | 2-methyl-benzothiazolyl | 264 dec | 0.16, III (9:1) | 94 |
| XXXVIII | methylthienyl | 272 dec | 0.13, III (9:1) | 61 |
| XXXIX | quinolinyl | 80 | 0.12, II (4:1) | 87 |
| XL | benzothiazolyl-S-CH₂ | — | 0.27, VI (100:10:4) | 26 |
| XLI | Br-thienyl-methyl | 258 dec. | — | 58 |
| XLII | 2-methyl-benzoxazolyl | 188 | 0.13, II (1:4) | 80 |

TABLE II-continued

![Structure: A—N attached to oxazolidinone with NH2xHCl]

| Ex. No. | A | Mp (°C.) | R_f / Eluent (ratio) | Yield (% of theory) |
|---------|---|----------|----------------------|---------------------|
| XLIII | H3C-benzothiazole | — | 0.05, II (1:1) | 57 |
| XLIV | Cl-benzothiophene | — | 0.5, I (100:3) | 79 |

EXAMPLE XLV (5S)-3-(3-Isopropyl-2-benzoxazolinon-6-yl)-5-aminomethyl-2-oxazolidinone Hydrochloride

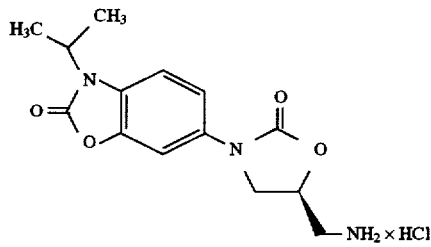

In analogy to the procedure of Example IV, starting from 3-benzyloxy-4-nitro-benzoic acid the corresponding azide is prepared (quant. yield). In analogy to the procedure of Example V, starting from 3-benzyloxy-4-nitrobenzoic acid azide, the corresponding butyl carbamate is prepared (yield: 63%; $R_f$ (VII, 95:5)=0.51).

3-Benzyloxy-1-butoxycarbonylamino-4-nitrobenzene is reacted analgously to the procedure of Example VI to give the corresponding oxazolidinone (yield: 73%; $R_f$ (II, 1:4)= 0.24).

In analogy to the procedures of Examples XXIII to XXVIII, starting from (5R)-3-(3-benzyloxy-4-nitrophenyl)-5-hydroxymethyl-3-oxazolidinone the corresponding amine is prepared (yields: 92%, 92% or 83%, $R_f$ (VIII, 85:10:5)= 0.08).

A mixture of (5S)-3-(3-benzyloxy-4-nitrophenyl)-5-aminomethyl-2-oxazolidinone (20.6 g, 0.06 mol) and di-tert-butyl dicarbonate (14.4 g, 0.066 mol) in dichloromethane (300 ml) is stirred at 0° C. for 14 h. The reaction mixture is concentrated and the product is precipitated using petroleum ether (yield: 25.4 g (95%), $R_f$ (I, 10:1)=0.80).

(5S)-3-(Benzyloxy-4-nitrophenyl)-5-(tert-butoxycarbonylaminoethyl)-2-oxazolidinone (25.3 g, 0.057 mol) in methanol/THF (2:3, 500 ml) is stirred under hydrogen (1 atm) with Pd/C (10%, 0.5 g) for 14 h. The catalyst is then filtered off and the solvents are stripped off (yield: 18.9 g (quant.), $R_f$ (I, 10:1)=0.28).

1M borane-tetrahydrofaran complex (64 ml, 64 mmol) is added at 0° C. to a mixture of (5S)-3-(4-amino-3-hydroxyphenyl)-5-(tert-butoxycarbonylaminomethyl)-2-oxazolidinone (18.9 g, 0.058 mol), acetone (8.6 ml, 0.116 mol) and THF (500 ml) and the mixture is stirred at room temperature for a further 24 h. The solution is treated with 1M sodium hydroxide (58 ml, 58 mmol), dried (Na_2SO_4) and the solvent is stripped off in vacuo (yield: 16.1 g (quant.), $R_f$ (I, 10:1)=0.53).

A solution of (5S)-3-(4-isopropylamino-3-hydroxyphenyl)-5-(tert-butoxycarbonylaminomethyl)-2-oxazolidinone (8.8 g, 24 mmol) and carbonyldiimidazole (CDI, 4.1 g, 25.2 g) in DMF (200 ml) is stirred at room temperature for 4 h. The mixture is added to ice-water and the deposited precipitate is filtered off with suction (yield: 9.0 g (96%), $R_f$ (I, 10:1)=0.71).

A suspension of (5S)-3-(isopropyl-2-benzothiazolinon-6-yl)-5-(tert-butoxycarbonylaminomethyl)-2-oxazolidinone (9.0 g, 23 mmol) and dioxane (200 ml) is treated with 4M HCl (in dioxane, 72 ml, 287 mmol) and stirred at room temperature for 14 h. The deposited precipitate is filtered off with suction, washed with ether, (2×) and dried.

Yield: 7.4 g (99%) MS(CI, NH_3): m/z=309 (M-Cl+NH_4^+)

$^1$H-NMR (200 MHz, [D_6]DMSO): δ=8.5 (bs, 3H, NH_3Cl), 7.62 (d, 1H, Ar-H), 7.45 (d, 1H, Ar-H), 7.25 (dd, 1H, Ar-H), 5.00 (m, 1H, 5-H), 4.45 (m, 1H, HCMe_2), 4.31 (t, 1H, 4-H), 3.90 (dd, 1H, 4-H), 3.20 (d, 2H, CH_2N), 1.45 (d, 6H, CH_3).

EXAMPLE XLVI (5S)-3-(3-Isopropyl-2-benzyloxazolinon-6-yl)-5-(benzyloxacetylaminomethyl)-2-oxazolidinone

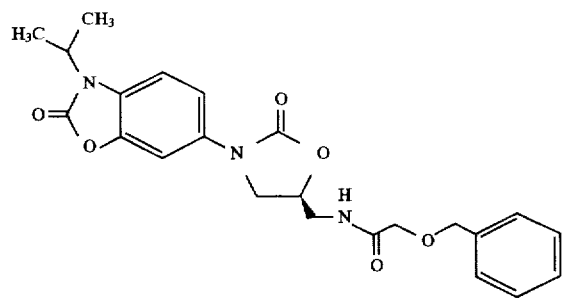

In analogy to the procedure of Example 3, starting from the corresponding hydrochloride (Example XLV) and benzyloxyacetyl chloride the title compound is prepared.

Yield: 93% $R_f$ (I, 10:1)=0.69

PREPARATION EXAMPLES

Example I (5S)-3-(5-[3-Pyridyl]-pyridin-2-yl)-5-(2-nitro-prop-1-en-1-yl-aminomethyl)-oxazolidin-2-one

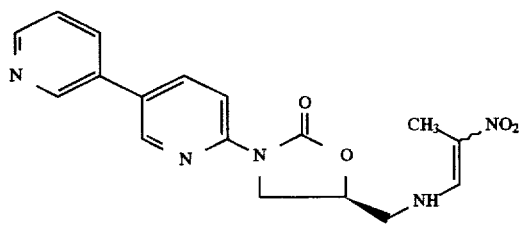

100 mg (0.37 mmol) of the compound from Example XXVIII (free base; prepared by dissolving in water, $NH_{3(aq)}$ addition to pH 11, extraction with $CH_2Cl_2$, drying over $MgSO_4$ and concentrating) are initially introduced into 1 ml of DMF under argon and 200 mg (1.11 mmol) of 2-(2-nitro-prop-1-en-1-yl-amino)-pyridine are added and the mixture is stirred overnight. It is treated with water, extracted 3× with ethyl acetate, and the organic phase is washed with satd. NaCl solution and dried over $MgSO_4$. It is concentrated and the residue is purified by column chromatography on silica gel (eluent $CH_2Cl_2$:MeOH=100:5). 126 mg (96% of theory) of the title compound are obtained.

M.p.: 207° C. $R_f$ value: ($CH_2Cl_2$:MeOH=10:1) 0.57 MS (DCI): 356 (M+H)$^+$ $^1$H-NMR (200 MHz, DMSO-d$_6$): δ=8.95 (d, J=2, 1H); 8.79 (d, J=2, 1H); 8.60 (dd, J=5, J=2, 1H); 8.4–7.9 and 7.6–7.4 (m, altogether 6H); 4.9 (m, 1H); 4.3 (m, 1H); 4.05 (m, 1H); 3.7 (m, 2H); 1.95 and 1.93 (s, altogether 3H).

Example 2

(5R)-3-(2-Methyl-benzo[4,5-d]thiazol-6-yl)-5-(2-thiazolyl-aminomethyl)-oxazolidin-2-one

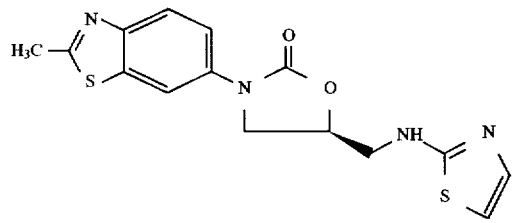

292 mg (2.92 mmol) of 2-aminothiazole are initially introduced into 5 ml of abs. THF under argon and are treated at −78° C. with 1.33 ml (2.92 mmol) of 2.2M n-BuLi solution. The mixture is stirred at −78° C. for 30 minutes. 0.5 g (1.46 mmol) of (5R)-3-(2-methyl-benzo[4,5-d]thiazol-6-yl)-5-methoxysulphonyloxymethyl-oxazolidin-2-one, dissolved in 5 ml of abs. THF, is added and the mixture is stirred at −78° C. for 1 h. The cooling bath is removed and the mixture is stirred overnight. $NH_4Cl$ solution and HCl solution (to pH 3) are added, and the mixture is extracted with chloroform, dried over $MgSO_4$ and concentrated. The substance is purified by column chromatography on silica gel (eluent $CH_2Cl_2$:MeOH=100:1 to 100:3). 193 mg (38% of theory) of the title compound are obtained.

M.p.: 207° C. $R_f$=0.47 ($CH_2Cl_2$:MeOH=10:1)

Example 3

(5R)-3-(5-(2-Pyridyl)-thien-2-yl)-5-thioacetylaminomethyl-oxazolidin-2-one

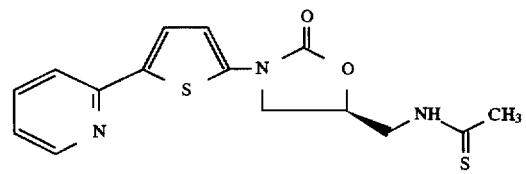

3.48 mg (1 mmol) of the compound from Example XXIX are treated with 4 ml of THF and 0.24 ml (1.7 mmol) of triethylamine. 152 µl (1.1 mmol) of ethyl dithioacetate are added with stirring to the reaction mixture thus obtained and it is kept at room temperature for 24 h. After concentrating, it is chromatographed on silica gel using methylene chloride/methanol (100:2).

Yield: 100 mg (36% of theory) M.p.: 181° C. dec. $R_f$ 0.36 (I; 100:5)

$^1$H-NMR (D$_6$-DMSO, 300 MHz): δ=10.37 (br, 1H); 8.47 (d, J=5 Hz, 1H); 7.75–7.88 (m, 2H); 7.62 (d, J=5 Hz, 1H); 7.2 (m, 1H); 6.58 (d, J=5 Hz, 1H); 5.03–5.13 (m, 1H); 4.21 (dd, J=10 Hz, 9 Hz, 1H); 3.95 (t, J=6 Hz, 2H); 3.85 (dd, J=10 Hz, 6 Hz, 1H); 2.45 (s, 3H).

The compounds listed in Table 1 are prepared analogously to the procedures of Examples 1 to 3:

TABLE 1

[Structure: A-N-C(=O)-O-CH(CH2-NH-R¹)-CH2- (oxazolidinone ring)]

| Ex. No. | A | R¹ | M.p. (°C.) | R_f, Eluent (ratio) | Yield (% of theory) |
|---|---|---|---|---|---|
| 4 | 5-(pyridin-2-yl)thien-2-yl | C(=S)NH-CH₃ | 160 dec. | 0.23, I (100:5) | 50 |
| 5 | 5-(pyridin-2-yl)thien-2-yl | C(=NH)CH₃ | 214 dec. | 0.02, I (100:5) | 40 |
| 6 | 5-(pyridin-2-yl)thien-2-yl | C(=O)CH₂OCH₃ | 127 | 0.29, I (100:5) | 80 |
| 7 | 5-(pyridin-2-yl)thien-2-yl | C(=NH)NH₂ | 212 dec. |  | 13 |
| 8 | 5-(pyridin-2-yl)thien-2-yl | C(=O)CH₂O-C₆H₅ | 152 | 0.32, I (100:5) | 79 |
| 9 | 5-(pyridin-2-yl)thien-2-yl | C(=S)NH₂ | 137 dec. |  | 25 |
| 10 | benzo[b]thien-2-yl (6-methyl) | C(=S)NH-CH₃ | 143 dec. |  | 99 |
| 11 | benzo[b]thien-2-yl (6-methyl) | C(=S)CH₂CH₃ | 142 dec. | 0.48, I (100:5) | 76 |
| 12 | 5-(pyridin-4-yl)thien-2-yl | C(=S)NH-CH₃ | 153 | 0.52, I (10:1) | 24 |
| 13 | 5-(pyridin-4-yl)thien-2-yl | C(=S)CH₃ | 159 | 0.57, I (10:1) | 30 |
| 14 | 5-(pyridin-3-yl)thien-2-yl | C(=S)NH-CH₃ |  | 0.48, I (10:1) | 5 |
| 15 | 5-(pyridin-3-yl)thien-2-yl | C(=S)CH₃ | 160 dec. | 0.58, I (10:1) | 28 |

TABLE 1-continued

Structure: A—N connected to oxazolidinone ring with CH₂—NH—R¹ substituent

| Ex. No. | A | R¹ | M.p. (°C.) | R_f, Eluent (ratio) | Yield (% of theory) |
|---|---|---|---|---|---|
| 16 | 5-Bromo-2-pyridyl | C(=NH)CH₃ | 160 | 0.11, I (85:15) | 54 |
| 17 | 2,6-dimethylpyridin-3-yl | C(=S)CH₃ | — | 0.11, I (97:3) | 58 |
| 18 | 6-methylpyridin-2-yl | C(=S)NHCH₃ | 91 | 0.59, I (9:1) | 39 |
| 19 | 6-phenylpyridazin-3-yl | C(=S)CH₃ | 189 | 0.53, I (9:1) | 48 |
| 20 | 3-methyl-2-oxo-benzothiazol-6-yl | C(=S)NHCH₃ | 190 | 0.44, I (9:1) | 63 |
| 21 | 2-methylbenzothiazol-6-yl | C(=S)NHCH₃ | 160 | 0.48, I (9:1) | 72 |
| 22 | 2-styryl-benzothiazol-6-yl | C(=S)NHCH₃ | 182 | 0.12, I (95:5) | 75 |
| 23 | 2-methylthio-benzothiazol-6-yl | C(=S)NHCH₃ | 152 | 0.31, I (9:1) | 52 |
| 24 | 3-thienyl | C(=S)NHCH₃ | 77 | 0.55, I (9:1) | 70 |
| 25 | quinolin-6-yl | C(=S)NHCH₃ | 115 | 0.51, I (9:1) | 71 |

TABLE 1-continued

Structure: A—N(C(=O)O—CH—CH₂—NH—R¹) cyclic carbamate with CH₂ bridge

| Ex. No. | A | R¹ | M.p. (°C.) | R_f, Eluent (ratio) | Yield (% of theory) |
|---|---|---|---|---|---|
| 26 | 2-(methylthio)-6-benzothiazolyl (CH₃—S—benzothiazole) | C(CH₃)=S (thioacetyl) | 163 dec. | 0.32, II (100:3) | 38 |
| 27 | 2-(methylthio)-6-benzothiazolyl | C(CH₃)=NH | 184 | — | 27 |
| 28 | 2-(methylthio)-6-benzothiazolyl | C(H)=NH | 203 | 0.08, VI (100:5:2) | 32 |
| 29 | 2-(methylthio)-6-benzothiazolyl | C(CH₃)=C(NO₂)CH₃ | 206 | 0.58 VII (10:1) | 68 |
| 30 | 6-benzothiazolyl | 2-thiazolyl-methylidene | 207 | 0.47, I (10:1) | 38 |
| 31 | 6-benzothiazolyl | 3-methylisoxazol-5-yl methylidene | 211 | 0.34, I (100:5) | 35 |
| 32 | 6-benzothiazolyl | 4-methylthiazol-2-yl methylidene | 201 | 0.49, I (100:5) | 29 |
| 33 | 6-benzothiazolyl | isoxazol-3-yl methylidene | 184 | 0.42, I (100:5) | 39 |
| 34 | 6-benzothiazolyl | thiazol-2-yl methylidene | 223 | 0.39, I (100:5) | 18 |
| 35 | 6-benzothiazolyl | 1,5-dimethylpyrazol-3-yl | 214 | 0.29, I (100:5) | 25 |
| 36 | 6-benzothiazolyl | 1-benzyl-5-methylpyrazol-3-yl | 218 | 0.39, I (100:5) | 39 |

TABLE 1-continued

Structure: A—N(C=O)—O ring (oxazolidinone) with CH2-NH-R¹ substituent

| Ex. No. | A | R¹ | M.p. (°C.) | R_f, Eluent (ratio) | Yield (% of theory) |
|---|---|---|---|---|---|
| 37 | 5-(6-methylpyridin-3-yl)pyridin-3-yl | C(CH₃)=N–CN | 229 | 0.28, I (100:5) | 37 |
| 38 | 5-bromo-2-thienyl | C(CH₃)=S | 133 dec. | 0.58, I (100:3) | 58 |
| 39 | 6-methylbenzothiazol-2-yl (CH) | C(CH₃)=S | 224 | — | 5 |
| 40 | 6-methylbenzoxazol-2-yl (CH) | C(CH₃)=S | 183 | — | 33 |
| 41 | 5-methylbenzothiazol-2-yl (CH) | C(CH₃)=S | 180 dec. | 0.31, I (100:3) | 45 |
| 42 | 3-methyl-6-methyl-2-oxo-benzothiazolin-2-yl | C(CH₃)=S | 203 dec. | 0.31, I (100:3) | 53 |
| 43 | 6-chloro-benzo[b]thiophen-2-yl | C(CH₃)=S | 176 dec. | 0.45, I (100:3) | 22 |
| 44 | 2-methyl-6-methylbenzothiazol-2-yl | CN | — | 0.75, I (10:1) | 49 |
| 45 | 5-(6-methylpyridin-3-yl)pyridin-3-yl | CN | 157 | 0.50, I (10:1) | 36 |
| 46 | 2-methyl-6-methylbenzothiazol-2-yl | C(CH₃)(=NH)NH₂ | >250 | — | 50 |
| 47 | 5-(6-methylpyridin-3-yl)pyridin-3-yl | C(CH₃)=NH | — | 0.07, VI (100:15:6) | 39 |

TABLE 1-continued $$A-N\underset{\underset{R^1}{NH}}{\overset{O}{\underset{\|}{C}}}O$$

| Ex. No. | A | R¹ | M.p. (°C.) | $R_f$, Eluent (ratio) | Yield (% of theory) |
|---|---|---|---|---|---|
| 48 | 2-methyl-6-yl-benzothiazole | C(CH₃)=NH | — | 0.07, VI, (100:15:6) | 28 |
| 49 | 2-methyl-6-yl-benzothiazole | C(CH₃)=N—C≡N | 239 | 0.36, I, (10:1) | 31 |
| 50 | 2-methyl-6-yl-benzothiazole | C(CH₃)=CH—NO₂ | 193 | 0.48, I, (10:1) | 67 |
| 51 | 2-methylthio-6-yl-benzothiazole | C(CH₃)=N—C≡N | 233 | 0.34, I, (100:5) | 36 |
| 52 | 2-methylthio-6-yl-benzothiazole | CN | 137 | 0.51, I, (10:1) | 38 |
| 53 | 3-isopropyl-2-oxo-benzoxazol-6-yl | C(CH₃)=NH | 208 | 0.4, I, (7:3) | 51 |
| 54 | 3-isopropyl-2-oxo-benzoxazol-6-yl | C(CH₃)=N—C≡N | >250 | 0.53, I, (10:1) | 16 |
| 55 | 2-methylthio-6-yl-benzothiazole | C(CH₃)(N(CH₃))=N—C≡N | 185 | 0.51, I, (10:1) | 51 |
| 56 | 3-isopropyl-2-oxo-benzoxazol-6-yl | C(CH₃)(N(CH₃))=N—C≡N | 233 | 0.43, I, (10:1) | 78 |
| 57 | 6-methyl-3-pyridyl-(5-methyl-2-thienyl) | C(=S)—NH—CH₃ | 180 dec. | 0.32, I, (10:1) | 11 |
| 58 | 6-propoxy-3-pyridyl-(5-methyl-2-thienyl) | C(=S)—NH—CH₃ | 148 dec. | 0.69, I, (10:1) | 64 |

TABLE 1-continued

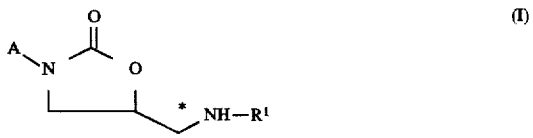

| Ex. No. | A | R¹ | M.p. (°C.) | $R_f$, Eluent (ratio) | Yield (% of theory) |
|---|---|---|---|---|---|
| 59 | H₃C—(CH₂)₂O—[pyridyl-thienyl] | —C(=S)—N(H)—CH₃ | 149 dec. | 0.54, I, (10:1) | 44 |
| 60 | H₃C—[pyridyl-thienyl] | —C(=S)—N(H)—CH₃ | 186 dec. | 0.52, I, (10:1) | 40 |
| 61 | H₅C₂—[pyridyl-thienyl] | —C(=S)—N(H)—CH₃ | 135 dec. | 0.67, I, (100:5) | 16 |
| 62 | H₃C—S—[benzothiazolyl-CH₃] | H₃C—C(=S)— | — | 0.46, I, (100:5) | 32 |

Example 63

(5S)-3-(3-Isopropyl-2-benzoxazolinon-6-yl)-5-hydroxyacetylamino-methyl-2-oxazolidinone

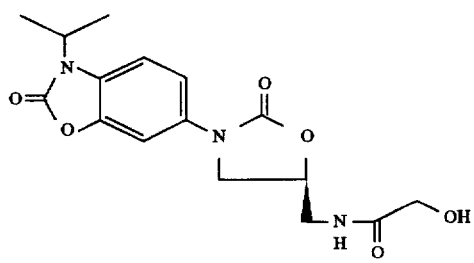

The compound from Example XLVI (390 mg, 0.89 mmol) in THF (10 ml) and ethyl acetate (10 ml) is stirred under 3 bar of hydrogen with Pd(OH)₂/C (5%, 30 mg). The catalyst is filtered off, the residue is washed with THF, the filtrate is concentrated and the residue is stirred with dichloromethane. 36 mg (11%) of the title compound are obtained as a white solid.

Yield: 11% $R_f$ value: (I, 10:1) 0.23 MS (CI): 367 (M+NH₄⁺)

¹H-NMR (200 MHz, [D₆]DMSO): δ=8.05 (bt, 1H), 7.62 (dd, 1H), 7.43 (d, 1H), 7.23 (dd, 1H), 5.60 (t, 1H, OH), 4.75 (m, 1H), 4.50 (m, 1H), 4.20 (t, 1H), 3.80 (m, 3H), 3.50 (m, 2H), 1.50 (d, 6H).

We claim:

1. Substituted oxazolidinones of the general formula (1)

$$\text{A-N(C(=O)O)-*-NH-R}^1 \quad (I)$$

in which

A represents a 5-membered aromatic heterocycle bonded directly via a carbon atom and having up to 3 heteroatoms from the series S, N and/or O, which can additionally have a fused benzene or naphthyl ring, or represents a 6-membered, aromatic heterocycle bonded directly via a carbon atom and having at least one nitrogen atom, or represents an in each case 6-membered, bi- or tricyclic aromatic radical bonded directly via a carbon atom and having at least one nitrogen-containing ring, or represents β-carbolin-3-yl or indolizinyl bonded directly via the 6-membered ring, the cyclic systems optionally in each case being substituted up to 3 times in an identical or different manner by carboxyl, halogen, cyano, mercapto, formyl, phenyl, trifluoromethyl, nitro, straight-chain or branched alkoxy, alkoxycarbonyl, alkylthio or acyl each having up to 6 carbon atoms or by straight-chain or branched alkyl or alkenyl each having up to 6 carbon atoms, which for their part can be substituted by phenyl, and/or being substituted by pyridyl, which for its part can be substituted by straight-chain alkyl or alkoxy each having up to 6 carbon atoms or represents a radical of the formula

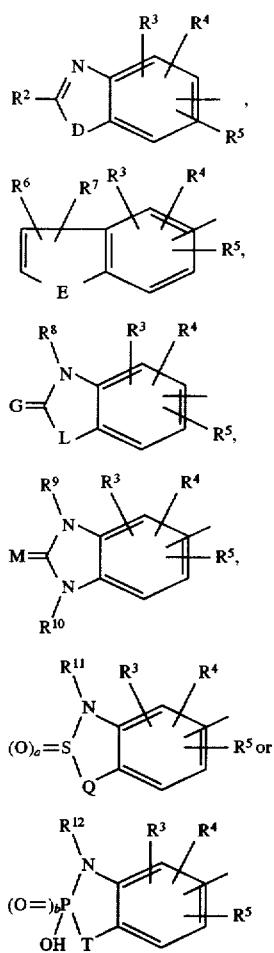

in which

R$^3$, R$^4$, R$^5$, R$^6$ and R$^7$ are identical or different and denote hydrogen or carboxyl, halogen, cyano, formyl, trifluoromethyl, nitro, straight-chain or branched alkyl having up to 6 carbon atoms or a group of the formula —CO—NR$^{13}$R$^{14}$, in which
R$^{13}$ and R$^{14}$ are identical or different and denote hydrogen, straight-chain or branched alkyl having up to 4 carbon atoms or phenyl, R$^2$, R$^9$, R$^{10}$, R$^{11}$ and R$^{12}$ are identical or different and denote hydrogen, cycloalkylcarbonyl or cycloalkyl each having 3 to 6 carbon atoms, or straight-chain or branched alkoxycarbonyl or alkylthio each having up to 6 carbon atoms, or denote straight-chain or branched alkyl having up to 10 carbon atoms, which is optionally substituted by cyano, trifluoromethyl, halogen, phenyl, hydroxyl, carboxyl, straight-chain or branched alkoxycarbonyl having up to 6 carbon atoms, aryl having 6 to 10 carbon atoms, cycloalkyl having 3 to 6 carbon atoms and/or by a group of the formula —(CO)$_c$—NR$^{15}$R$^{16}$, R$^{17}$—N—SO$_2$—R$^{18}$, R$^{19}$R$^{20}$—N—SO$_2$— or R$^{21}$—S(O)$_d$-, in which c denotes a number 0 or 1, R$^{15}$, R$^{16}$ and R$^{17}$ have the meaning of R$^{13}$ and R$^{14}$ indicated above and are identical to or different from this, or together with the nitrogen atom form a 5- to 6-membered, saturated heterocycle optionally having a further heteroatom from the series N, S and/or O, which for its part can be optionally substituted, also on a further nitrogen atom, by straight-chain or branched alkyl or acyl having up to 3 carbon atoms, R$^{19}$ and R$^{20}$ have the meaning of R$^{13}$ and R$^{14}$ indicated above and are identical to or different from this, d denotes a number 0, 1 or 2, R$^{18}$ and R$^{21}$ are identical or different and denote straight-chain or branched alkyl having up to 4 carbon atoms, benzyl, phenyl or tolyl, or denote straight-chain or branched acyl having up to 6 carbon atoms, which is optionally substituted by trifluoromethyl, trichloromethyl or by a group of the formula —OR$^{22}$, in which R$^{22}$ denotes hydrogen or straight-chain or branched alkyl having up to 6 carbon atoms, which is optionally substituted by aryl having up to 10 carbon atoms, or denotes a group of the formula —(CO)$_e$—NR$^{23}$R$^{24}$, —NR$^{25}$—SO$_2$R$^{26}$, R$^{27}$R$^{28}$—NSO$_2$— or R$^{29}$—S(O)$_f$, in which e has the meaning of c indicated above and is identical to or different from this, R$^{23}$ and R$^{24}$ and R$^{25}$ each have the meaning of R$^{15}$, R$^{16}$ and R$^{17}$ indicated above and are identical to or different from this, R$^{27}$ and R$^{28}$ have the meaning of R$^{13}$ and R$^{14}$ indicated above and are identical to or different from this, f has the meaning of d indicated above and is identical to or different from this, R$^{26}$ and R$^{29}$ have the meaning of R$^{18}$ and R$^{21}$ in each case indicated above and are identical to or different from this, D denotes an oxygen atom or a radical of the formula —S(O)$_g$, in which g denotes a number 0, 1 or 2, E and L are identical or different and denote an oxygen or a sulphur atom, G, M, T and Q are identical or different and denote an oxygen or a sulphur atom, or a group of the formula —NR$^{30}$, in which R$^{30}$ denotes hydrogen or straight-chain or branched alkyl having up to 5 carbon atoms, a and b are identical or different and denote a number 1 or 2, R$^1$ represents a radical of the formula

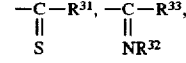

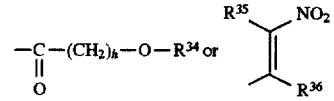

in which

R$^{31}$ denotes straight-chain or branched alkyl having up to 7 carbon atoms, cycloalkyl having 3 to 6 carbon atoms, phenyl or a group of the formula —NR$^{38}$R$^{39}$, in which
R$^{38}$ and R$^{39}$ have the meaning of R$^{13}$ and R$^{14}$ indicated above and are identical to or different from this, R$^{32}$ denotes hydrogen, cyano, cycloalkyl having 3 to 6 carbon atoms, phenyl or straight-chain or branched alkyl having up to 7 carbon atoms, R$^{33}$ denotes hydrogen, straight-chain or branched alkyl having up to 7 carbon atoms, phenyl, cycloalkyl having 3 to 6 carbon atoms or a group of the formula —NR$^{40}$R$^{41}$, in which
R$^{40}$ and R$^{41}$ have the meaning of R$^{13}$ and R$^{14}$ indicated above and are identical to or different from this,

47 h denotes a number 1, 2, 3 or 4, $R^{34}$ denotes hydrogen, straight-chain or branched alkyl having up to 6 carbon atoms or benzyl, $R^{35}$ and $R^{36}$ are identical or different and denote hydrogen or straight-chain or branched alkyl having up to 6 carbon atoms, or $R^1$ represents cyano or a 5- to 7-membered, saturated, partially unsaturated or unsaturated heterocycle having up to 3 heteroatoms from the series S, N and/or O, which is optionally substituted, also via an N function, up to 2 times in an identical or different manner by benzyl, halogen or by straight-chain or branched alkyl having up to 5 carbon atoms, and their stereoisomers, stereoisomer mixtures and salts.

2. Compounds of the general formula (I) according to claim 1, in which

A represents quinolyl, benzothiophenyl, benzothiazolyl, benzoxazolyl, pyridyl, pyridazyl or thienyl, each bonded via a carbon atom, each of which is optionally substituted up to 3 times in an identical or different manner by fluorine, chlorine, bromine, phenyl or by straight-chain or branched alkyl or alkylthio each having up to 4 carbon atoms or by straight-chain or branched alkenyl having up to 4 carbon atoms, which for its part can be substituted by phenyl, and/or is substituted by pyridyl, which for its part can be substituted by straight-chain or branched alkyl or alkoxy each having up to 5 carbon atoms, or represents a radical of the formula

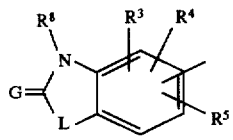

in which

G denotes an oxygen or sulphur atom,

L denotes an oxygen or sulphur atom, $R^8$ denotes straight-chain or branched alkyl or alkylthio each having up to 6 carbon atoms, $R^3$, $R^4$ and $R^5$ are identical or different and denote hydrogen, fluorine, chlorine or bromine, $R^1$ represents a radical of the formula

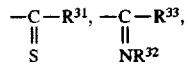

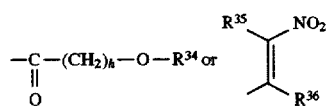

in which $R^{31}$ denotes straight-chain or branched alkyl having up to 5 carbon atoms, cyclopropyl, cyclobutyl, cyclopentyl, cyclohexyl, phenyl or a group of the formula —$NR^{38}R^{39}$, in which $R^{38}$ and $R^{39}$ are identical or different and denote hydrogen, methyl or ethyl, $R^{32}$ denotes hydrogen, cyano, cyclopropyl, cyclobutyl, cyclopentyl, cyclohexyl, phenyl or straight-chain or branched alkyl having up to 5 carbon atoms, $R^{33}$ denotes hydrogen, straight-chain or branched alkyl having up to 5 carbon atoms, phenyl, cyclopropyl, cyclobutyl, cyclopentyl, cyclohexyl or a group of the formula —$NR^{40}R^{41}$, in which

48

$R^{40}$ and $R^{41}$ have the meaning of $R^{38}$ and $R^{39}$ given above and are identical to or different from this, h denotes a number 1, 2, 3 or 4, $R^{34}$ denotes hydrogen, straight-chain or branched alkyl having up to 4 carbon atoms or benzyl, $R^{35}$ and $R^{36}$ are identical or different and denote hydrogen or straight-chain or branched alkyl having up to 4 carbon atoms, or $R^1$ represents cyano or thienyl, oxazolyl, thiazolyl, isoxazolyl or pyrazolyl, each of which is optionally substituted, also via an N function, up to 2 times in an identical or different manner by benzyl, fluorine, chlorine, bromine or by straight-chain or branched alkyl having up to 3 carbon atoms, and their stereoisomers, stereoisomer mixtures and salts.

3. Compounds of the general formula (I) according to claim 1, in which

A represents quinolyl, benzothiophenyl, benzothiazolyl, benzoxazolyl, pryidyl, pyridazyl or thienyl, each bonded via a carbon atom, each of which is optionally substituted up to 2 times in an identical or different manner by fluorine, chlorine, bromine, phenyl, by straight-chain or branched alkyl or alkylthio each having up to 3 carbon atoms or by straight-chain or branched alkenyl having up to 3 carbon atoms, which for its part can be substituted by phenyl, and/or is substituted by pyridyl, which for its part can be substituted by straight-chain or branched all or alkoxy each having up to 4 carbon atoms, or represents a radical of the formula

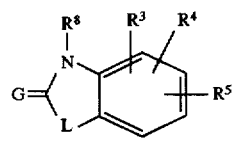

in which

G denotes an oxygen or sulphur atom,

L denotes an oxygen or sulphur atom, $R^8$ denotes straight-chain or branched alkyl having up to 4 carbon atoms, $R^3$, $R^4$ and $R^5$ are identical or different and denote hydrogen, fluorine, chlorine or bromine, $R^1$ represents a radical of the formula

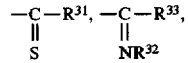

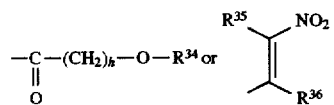

in which $R^{31}$ denotes straight-chain or branched alkyl having up to 4 carbon atoms, cyclopropyl, cyclobutyl, cyclopentyl, cyclohexyl, phenyl or a group of the formula —$NR^{38}R^{39}$, in which $R^{38}$ and $R^{39}$ are identical or different and denote hydrogen or methyl, $R^{32}$ denotes hydrogen, cyano, cyclopropyl, cyclobutyl, cyclopentyl, cyclohexyl, phenyl or straight-chain or branched alkyl having up to 4 carbon atoms, $R^{33}$ denotes hydrogen, straight-chain or branched alkyl having up to 4 carbon atoms, phenyl, cyclopropyl, cyclobutyl, cyclopentyl, cyclohexyl or a group of the formula —NR⁴⁰R⁴¹, in which R⁴⁰ and R⁴¹ have the meaning of R³⁸ and R³⁹ given above and are identical to or different from this, h denotes a number 1, 2, 3 or 4, R³⁴ denotes hydrogen, straight-chain or branched alkyl having up to 3 carbon atoms or benzyl, R³⁵ and R³⁶ are identical or different and denote hydrogen or straight-chain or branched alkyl having up to 3 carbon atoms, or R¹ represents cyano or thienyl, thiazolyl, isoxazolyl or pyrazolyl, each of which can optionally be substituted, also via an N function, up to 2 times in an identical or different manner by benzyl, fluorine, chlorine, bromine or by straight-chain or branched alkyl having up to 3 carbon atoms, and their stereoisomers, stereoisomer mixtures and salts.

4. Compounds of the general formula (I) according to claim 1, selected from the group consisting of:

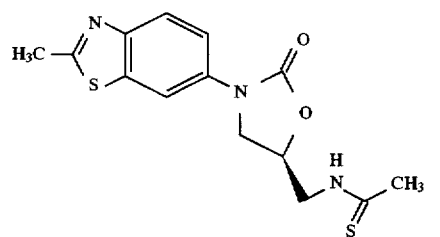

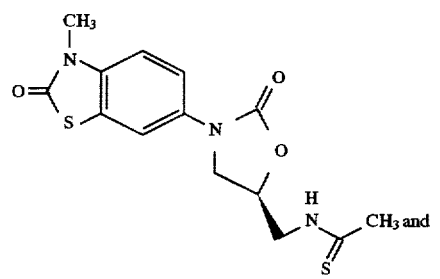

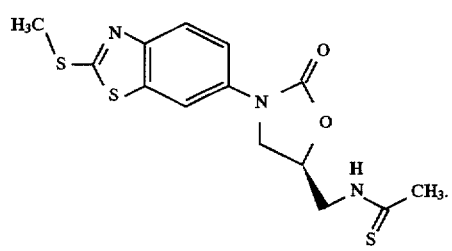

5. A process for preparing a compound according to claim 1, said process comprising:

a) reacting a compound of the formula (II):

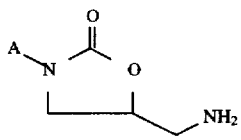  (II)

in which

A has the meaning indicated in claim 1;

with a compound of the general formula (III):

  (III)

in which

R¹ has the meaning indicated in claim 1; and

Y is selected from the group consisting of hydrogen, halogen or straight-chain or branched alkoxy or alkoxycarbonyloxy; or b) reacting a compound of the formula (IV):

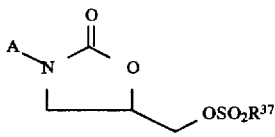  (IV)

in which

A has the meaning indicated in claim 1; and

R³⁷ represents C₁₋₄-alkyl;

with a compound of the formula (V):

  (V)

in which

R¹' represents a R¹ heterocycle according to claim 1; or with ethyl dithioacetate in an inert solvent, and, optionally, in the presence of a base.

6. The process according to claim 5, further comprising oxidation of the product of a) or b) to yield the corresponding S-oxide.

7. The process according to claim 5, further comprising resolution of a racemic product of a) or b) to yield purified stereoisomers.

8. An antibacterial composition comprising an antibacterially effective amount of an oxazolidinone or a stereoisomer, stereoisomer mixture or salt thereof according to claim 1 and a pharmaceutically acceptable carrier.

9. A method of treating bacterial infections in a host in need thereof which comprises administering an effective amount of a compound according to claim 1 to said host.

* * * * *